United States Patent [19]
Hulin et al.

[11] Patent Number: 5,998,463
[45] Date of Patent: Dec. 7, 1999

[54] GLYCOGEN PHOSPHORYLASE INHIBITORS

[75] Inventors: Bernard Hulin, Essex; Reinhard Sarges, Mystic, both of Conn.

[73] Assignee: Pfizer Inc, New York, N.Y.

[21] Appl. No.: 09/251,141

[22] Filed: Feb. 16, 1999

Related U.S. Application Data

[60] Provisional application No. 60/076,132, Feb. 27, 1998.

[51] Int. Cl.⁶ .......................... A01N 43/38; C07D 209/34
[52] U.S. Cl. ............................................ 514/418; 548/486
[58] Field of Search .............................. 548/486; 514/418

[56] References Cited

FOREIGN PATENT DOCUMENTS

| | | | |
|---|---|---|---|
| 96/39384 | 12/1996 | WIPO . | |
| 9639384 | 12/1996 | WIPO ........................... | C07D 209/42 |
| 9639385 | 12/1996 | WIPO ........................... | C07D 209/42 |

*Primary Examiner*—Johann Richter
*Assistant Examiner*—Dominic Keating
*Attorney, Agent, or Firm*—Peter C. Richardson; Gregg C. Benson; Martha A. Gammill

[57] ABSTRACT

This invention relates to certain 5-acyl-2-oxo-indole-3-carboxamides useful as inhibitors of glycogen phosphorylase, methods of treating glycogen phosphorylase dependent diseases or conditions with such compounds and pharmaceutical compositions comprising such compounds. This invention also relates to pharmaceutical compositions comprising those 5-acyl-2-oxo-indole-3-carboxamides in combination with antidiabetes agents and methods of treating glycogen phosphorylase dependent diseases or conditions with such compositions.

23 Claims, No Drawings

GLYCOGEN PHOSPHORYLASE INHIBITORS

This application is a continuation of U.S. Provisional Application No. 60/076,132 filed Feb. 27, 1998.

BACKGROUND OF THE INVENTION

This invention relates to glycogen phosphorylase inhibitors, pharmaceutical compositions containing such inhibitors and the use of such inhibitors to treat diabetes, hyperglycemia, hypercholesterolemia, hypertension, hyperinsulinemia, hyperlipidemia, atherosclerosis, myocardial ischemia and other tissue ischemias in animals, particularly mammals. In particular, this invention relates to certain 5-acyl-2-oxo-indole-3-carboxamides having such glycogen phosphorylase inhibitor activity.

In spite of the early discovery of insulin and its subsequent widespread use in the treatment of diabetes, and the later discovery of and use of sulfonylureas (e.g., Chlorpropamide™ Pfizer), Tolbutamide™ (Upjohn), Acetohexamide™ (E. I. Lilly), Tolazamide™ (Upjohn)) and biguanides (e.g., Phenformin™ (Ciba Geigy), Metformin™ (G. D. Searle)), alpha-glucosidase inhibitors (e.g., glucophage) and insulin sensitizing agents (e.g., troglitazone) as oral hypoglycemic agents, there is still a need for improved diabetes therapies. The use of insulin, necessary in about 10% of diabetic subjects in which synthetic hypoglycemic agents are not effective (Type I diabetes, insulin dependent diabetes mellitus), requires multiple daily doses, usually by self injection. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type 2 diabetes, NIDDM) usually consists of a combination of diet, exercise, oral agents, e.g. sulfonylureas, and in more severe cases, insulin. However, the clinically available hypoglycemics can have other side effects which limit their use. In any event, where one of these agents may fail in an individual case, another may succeed. A continuing need for hypoglycemic agents, which may have fewer side effects or succeed where others fail, is clearly evident.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque", which consists of accumulated intimal smooth muscle cells laden with lipid and surrounded by extracellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particular high risk. Other independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition which occurs in the human population as a secondary symptom to various other disorders such as renal artery stenosis, pheochromocytoma or endocrine disorders. However, hypertension is also evidenced in many subjects in whom the causative agent or disorder is unknown. While such "essential" hypertension is often associated with disorders such as obesity, diabetes and hypertriglyceridemia, the relationship between these disorders has not been elucidated. Additionally, many subjects display the symptoms of high blood pressure in the complete absence of any other signs of disease or disorder.

It is known that hypertension can directly lead to heart failure, renal failure and stroke (brain hemorrhaging). These conditions are capable of causing rapid death in a subject. Hypertension can also contribute to the development of atherosclerosis and coronary disease. These conditions gradually weaken a subject, leading to eventual death due to cardiovascular failure.

The exact cause of essential hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus, a broad range of beta-blockers, vasoconstrictors, angiotensin converting enzyme inhibitors and the like have been developed and marketed as antihypertensives. The treatment of hypertension utilizing these compounds has proven beneficial in the prevention of deaths resulting from little or no periods of illness such as heart failure, renal failure and brain hemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries;

while sodium retention increases blood volume. Thus, the lowering of insulin levels in hyperinsulinemics can prevent abnormal vascular growth and renal sodium retention caused by high insulin levels and thereby alleviate hypertension.

Cardiac hypertrophy is a significant risk factor in the development of sudden death, myocardial infarction, and congestive heart failure. These cardiac events are due, at least in part, to increased susceptibility to myocardial injury after ischemia and reperfusion which can occur in out-subject as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million subjects undergoing non-cardiac surgery are considered to be at risk, with incidences of perioperative death and serious cardiac complications as high as 20–25% in some series. In addition, of the 400,000 subjects undergoing coronary by-pass surgery annually, perioperative myocardial infarction is estimated to occur in 5% and death in 1–2%. There is currently a need for improved drug therapy which reduces damage to cardiac tissue from perioperative myocardial ischemia or enhances cardiac resistance to ischemic episodes. If such a therapy were found, it would be expected to reduce hospitalizations, enhance quality and length of life and reduce overall health care costs of high risk subjects.

Hepatic glucose production is an important target for Type 2 therapy. The liver is the major regulator of plasma glucose levels in the post absorptive (fasted) state, and the rate of hepatic glucose production in Type 2 diabetic subjects is significantly elevated relative to normal individuals. Likewise, in the postprandial or fed state, where the liver has a proportionately smaller role in the total plasma glucose supply, hepatic glucose production is abnormally high in Type 2 diabetic subjects.

Glycogenolysis is an important target for interruption of hepatic glucose production. The liver produces glucose by glycogenolysis (breakdown of the glucose polymer glycogen) and gluconeogenesis (synthesis of glucose from 2- and 3-carbon precursors). Several lines of evidence indicate that glycogenolysis may make an important contribution to hepatic glucose output in Type 2 diabetes. First, in normal post absorptive humans, up to 75% of hepatic glucose production is estimated to result from glycogenolysis. Second, subjects having liver glycogen storage diseases, including Hers' disease (glycogen phosphorylase deficiency), display episodic hypoglycemia. These observations suggest that glycogenolysis may be a significant process for hepatic glucose production.

Glycogenolysis is catalyzed in liver, muscle, and brain by tissue-specific isoforms of the enzyme glycogen phosphorylase. This enzyme cleaves the glycogen macromolecule to release glucose-1-phosphate and a new shortened glycogen macromolecule. Two types of glycogen phosphorylase inhibitors have been reported to date: glucose and glucose analogs [Martin, J. L. et al. *Biochemistry*, 1991, 30, 10101] and caffeine and other purine analogs [Kasvinsky, P. J. et al. *J. Biol. Chem.*, 1978, 253, 3343–3351 and 9102–9106]. These compounds, and glycogen phosphorylase inhibitors in general, have been postulated to be of potential use for the treatment of Type 2 diabetes by decreasing hepatic glucose production and lowering glycemia. [Blundell, T. B. et al. *Diabetologia*, 1992, 35, Suppl. 2, 569–576 and Martin et al. Biochemistry 1991, 30, 10101].

WO96/39385 discloses certain substituted N-(indole-2-carbonyl)-B-alanimamides and derivatives as antidiabetic agents. WO96/39384 discloses certain substituted N-(indole-2-carbonyl)-glycinamides and derivatives as antidiabetic agents.

The mechanism(s) responsible for the myocardial or other tissue injury observed after ischemia and reperfusion is not fully understood. It has been reported (M. F. Allard, et al. Am. J. Physiol. 267, H66–H74, 1994) that "pre ischemic glycogen reduction . . . is associated with improved post ischemic left ventricular functional recovery in hypertrophied rat hearts".

Thus, although there are a variety of hyperglycemia, hypercholesterolemia, hypertension, hyperlipidemia, atherosclerosis and myocardial ischemia therapies, there is a continuing need and a continuing search in this field of art for alternative therapies.

SUMMARY OF THE INVENTION

This invention is directed to glycogen phosphorylase inhibitor compounds of Formula I which are useful for the treatment of diabetes, hyperglycemia, hypercholesterolemia, hypertension, hyperinsulinemia, hyperlipidemia, atherosclerosis and myocardial or other tissue ischemia.

This invention is particularly directed to compounds of Formula I

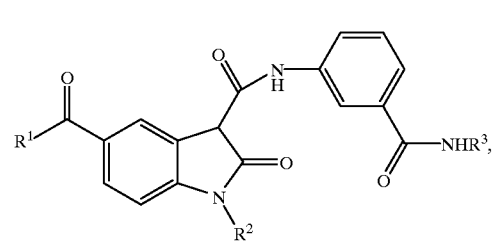

prodrugs thereof and pharmaceutically acceptable salts of said compounds and said prodrugs wherein:

$R^1$ is $(C_1-C_4)$alkyl, $(C_3-C_7)$cycloalkyl, phenyl or phenyl independently substituted with up to three $(C_1-C_4)$ alkyl, $(C_1-C_4)$alkoxy or halogen;

$R^2$ is $(C_1-C_4)$alkyl optionally substituted with up to three fluoro atoms; and $R^3$ is $(C_3-C_7)$cycloalkyl; phenyl; phenyl substituted at the para position with $(C_1-C_4)$alkyl, halo or trifluoromethyl; phenyl substituted at the meta position with fluoro; or phenyl substituted at the ortho position with fluoro.

A first group of preferred compounds of Formula I are the compounds of Formula I, prodrugs thereof and pharmaceutically acceptable salts of said compounds and said prodrugs wherein $R^1$ is phenyl; $R^2$ is ethyl; and $R^3$ is phenyl, phenyl substituted at the para position with $(C_1-C_4)$alkyl, halo or trifluoromethyl, phenyl substituted at the meta position with fluoro, or phenyl substituted at the ortho position with fluoro.

A second group of preferred compounds of Formula I are the compounds of Formula I, prodrugs thereof and pharmaceutically acceptable salts of said compounds and said prodrugs wherein $R^1$ is methyl and $R^2$ is ethyl.

A more preferred group of compounds, hereinafter termed the third group of preferred compounds, within the second preferred group of compounds are those compounds of the second group of preferred compounds of Formula I, prodrugs thereof and pharmaceutically acceptable salts of said compounds and said prodrugs wherein $R^3$ is phenyl, phenyl substituted at the para position with $(C_1-C_4)$alkyl, halo or trifluoromethyl, phenyl substituted at the meta position with fluoro, or phenyl substituted at the ortho position with fluoro.

An especially preferred group of compounds within the third preferred group of compounds are 5-acetyl-1-ethyl-2-oxo-2,3-dihydro-1H-indole-3-carboxylic acid (3-p-tolylcarbamoyl-phenyl)-amide; 5-acetyl-1-ethyl-2-oxo-2,3-dihydro-1H-indole-3-carboxylic acid (3-(4-bromophenylcarbamoyl-phenyl)-amide; and 5-acetyl-1-ethyl-2-oxo-2,3-dihydro-1H-indole-3-carboxylic acid (3-phenylcarbamoyl-phenyl)-amide.

A particularly preferred compound within the third group of compounds is the compound wherein $R^3$ is p-tolyl.

Another particularly preferred compound within the third group of compounds is the compound wherein $R^3$ is 4-bromophenyl.

Yet another particularly preferred compound within the third group of compounds is the compound wherein $R^3$ is phenyl.

Yet another aspect of this invention is directed to a method for treating a glycogen phosphorylase dependent disease or condition in an animal, particularly a mammal, by administering to said animal suffering from a glycogen phosphorylase dependent disease or condition a glycogen phosphorylase dependent disease or condition treating amount of a Formula I compound, a prodrug thereof or a pharmaceutically acceptable salt of said compound or said prodrug.

Yet another aspect of this invention is directed to a method for treating hyperglycemia in an animal, particularly a mammal, by administering to said animal suffering from hyperglycemia a hyperglycemia treating amount of a Formula I compound, a prodrug thereof or a pharmaceutically acceptable salt of said compound or said prodrug.

Yet another aspect of this invention is directed to a method for treating diabetes in an animal, particularly a mammal, by administering to said animal suffering from diabetes a diabetes treating amount of a Formula I compound, a prodrug thereof or a pharmaceutically acceptable salt of said compound or said prodrug. Included in the treatment of diabetes is the prevention or attenuation of long term complications such as, but not limited to, neuropathy, nephropathy, retinopathy or cataracts.

Yet another aspect of this invention is directed to a method for treating hypercholesterolemia in an animal, particularly a mammal, by administering to said animal suffering from hypercholesterolemia a hypercholesterolemia treating amount of a Formula I compound, a prodrug thereof or a pharmaceutically acceptable salt of said compound or said prodrug.

Yet another aspect of this invention is directed to a method for treating atherosclerosis in an animal, particularly a mammal, by administering to said animal suffering from or susceptible to atherosclerosis an atherosclerosis treating amount of a Formula I compound, a prodrug thereof or a pharmaceutically acceptable salt of said compound or said prodrug.

Yet another aspect of this invention is directed to a method for treating hyperinsulinemia in an animal, particularly a mammal, by administering to said animal suffering from hyperinsulinemia a hyperinsulinemia treating amount of a Formula I compound, a prodrug thereof or a pharmaceutically acceptable salt of said compound or said prodrug.

Yet another aspect of this invention is directed to a method for treating hypertension in an animal, particularly a mammal, by administering to said animal suffering from hypertension a hypertension treating amount of a Formula I compound, a prodrug thereof or a pharmaceutically acceptable salt of said compound or said prodrug.

Yet another aspect of this invention is directed to a method for treating hyperlipidemia in an animal, particularly a mammal, by administering to said animal suffering from hyperlipidemia a hyperlipidemia treating amount of a Formula I compound, a prodrug thereof or a pharmaceutically acceptable salt of said compound or said prodrug. Included in the treatment of hyperlipidemia is the lowering of triglycerides and free fatty acids.

Yet another aspect of this invention is directed to a method for treating or preventing a tissue ischemic injury in an animal, particularly a mammal, by administering to said animal a tissue ischemic injury preventing amount of a Formula I compound, a prodrug thereof or a pharmaceutically acceptable salt of said compound or said prodrug. Included within tissue ischemic injury is ischemic injury due to organ transplant.

Yet another aspect of this invention is directed to a method for treating or preventing a myocardial ischemic injury in an animal, particularly a mammal, by administering to said animal at risk for myocardial ischemic injury a myocardial ischemic injury treating or preventing amount of a Formula I compound, a prodrug thereof or a pharmaceutically acceptable salt of said compound or said prodrug.

Yet another aspect of this invention is directed to a method for treating or preventing a perioperative myocardial ischemic injury in an animal, particularly a mammal, by administering to said animal at risk for perioperative myocardial ischemic injury a perioperative myocardial ischemic injury treating or preventing effective amount of a Formula I compound, a prodrug thereof or a pharmaceutically acceptable salt of said compound or said prodrug.

This invention is also directed to pharmaceutical compositions which comprise a therapeutically effective amount of a compound of Formula I, a prodrug thereof or a pharmaceutically acceptable salt of said compound or said prodrug and a pharmaceutically acceptable carrier or diluent.

Preferred compositions include pharmaceutical compositions for the treatment of glycogen phosphorylase dependent diseases or conditions in animals, particularly mammals, which comprise a glycogen phosphorylase dependent disease or condition treating amount of a compound of Formula I, a prodrug thereof or a pharmaceutically acceptable salt of said compound or said prodrug and a pharmaceutically acceptable carrier or diluent.

Preferred pharmaceutical compositions within the immediately preceding group are those compositions wherein the glycogen phosphorylase inhibitor is a compound of Formula I.

Another aspect of this invention is directed to pharmaceutical compositions for the treatment of diabetes which comprise a therapeutically effective amount of a glycogen phosphorylase inhibitor of Formula I;

one or more antidiabetic agents such as insulin and insulin analogs (e.g. LysPro insulin); GLP-1 (7-37) (insulinotropin) and GLP-1 (7-36)-NH$_2$; sulfonylureas and analogs such as chlorpropamide, glibenclamide, tolbutamide, tolazamide, acetohexamide, glipizide, glimepiride, repaglinide and meglitinide); biguanides such as mefformin, phenformin and buformin; $\alpha_2$-antagonists and imidazolines such as midaglizole, isaglidole, deriglidole, idazoxan, efaroxan and fluparoxan; other insulin secretagogues such as linogliride and A-4166; glitazones such as ciglitazone, pioglitazone, englitazone, troglitazone, darglitazone and BRL49653; aldose reductase inhibitors such as epalrestat, sorbinil, tolrestat and zopolrestat; sorbitol dehydrogenase inhibitors; fatty acid oxidation inhibitors such as clomoxir and etomoxir; α-glucosidase inhibitors such as acarbose, miglitol, emiglitate, voglibose, MDL-25,637, camiglibose and MDL-73, 945; β-agonists such as (4-(2-(2-( 6-aminopyridin-3-yl)-2(R)-hydroxyethylamino)ethoxy)phenyl)acetic acid and BRL 35135, BRL 37344, Ro 16-8714, ICI D7114 and CL 316,243; phosphodiesterase inhibitors such as L-386,398; lipid-lowering agents such as benfluorex; antiobesity agents such as fenfluramine, sibutramine and bromocriptine; vanadate and vanadium complexes (e.g. naglivan) and peroxovanadium complexes; amylin antagonists; glucagon antagonists; growth hormone secretagogues; gluconeogenesis inhibitors such as glucose-6-phosphatase inhibitors; somatostatin analogs; antilipolytic agents such as nicotinic acid, acipimox and WAG 994; prodrugs thereof or pharmaceutically acceptable salts of said antidiabetic agents or said prodrugs and a pharmaceutically acceptable carrier or diluent.

Another aspect of this invention is directed to a method for treating glycogen phosphorylase dependent diseases or conditions in an animal, particularly a mammal, which comprises administering to said animal suffering from a glycogen phosphorylase dependent disease or condition a glycogen phosphorylase dependent disease or condition treating amount of a composition set forth in the immediately preceding paragraph.

Another aspect of this invention is a method of treating diabetes in an animal, particularly a mammal, with the above described combination compositions.

Another aspect of this invention is directed to a kit comprising a. an amount of a compound of Formula I, a prodrug thereof or a pharmaceutically acceptable salt of said compound or said salt in a first unit dosage form;

b. an amount of an antidiabetic agent such as insulin and insulin analogs (e.g. LysPro insulin); GLP-1 (7-37) (insulinotropin) and GLP-1 (7-36)-NH$_2$; sulfonylureas and analogs such as chlorpropamide, glibenclamide, tolbutamide, tolazamide, acetohexamide, glipizide, glimepiride, repaglinide and meglitinide; biguanides such as metformin, phenformin and buformin; α$_2$-antagonists and imidazolines such as midaglizole, isaglidole, deriglidole, idazoxan, efaroxan and fluparoxan; other insulin secretagogues such as linogliride and A4166; glitazones such as ciglitazone, pioglitazone, englitazone, troglitazone, darglitazone and BRL49653; aldose reductase inhibitors such as epalrestat, sorbinil, tolrestat and zopolrestat; fatty acid oxidation inhibitors such as clomoxir and etomoxir; α-glucosidase inhibitors such as acarbose, miglitol, emiglitate, voglibose, MDL-25,637, camiglibose and MDL-73,945; β-agonists such as (4-(2-(2-(6-aminopyridin-3-yl)- 2(R)-hydroxyethylamino)ethoxy) phenyl)acetic acid and BRL 35135, BRL 37344, Ro 16-8714, ICI D7114 and CL 316,243; phosphodiesterase inhibitors such as L-386,398; lipid-lowering agents such as benfluorex; antiobesity agents such as fenfluramine, sibutramine and bromocriptine; vanadate and vanadium complexes (e.g. naglivan) and peroxovanadium complexes; amylin antagonists; glucagon antagonists; growth hormone secretagogues; gluconeogenesis inhibitors such as glucose-6-phosphatase inhibitors; somatostatin analogs; antilipolytic agents such as nicotinic acid, acipimox and WAG 994; prodrugs thereof or pharmaceutically acceptable salts of said antidiabetic agents or said prodrugs and a pharmaceutically acceptable carrier or diluent in a second unit dosage form; and c. a container.

Another aspect of this invention is directed to a compound of formula II,

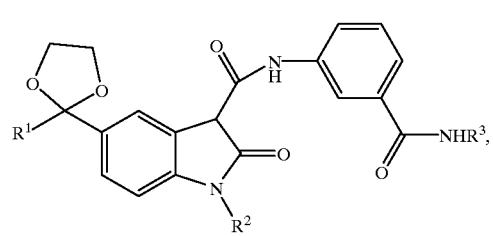

wherein:

$R^1$ is ($C_1$–$C_4$)alkyl, ($C_3$–$C_7$)cycloalkyl, phenyl or phenyl independently substituted with up to three ($C_1$–$C_4$) alkyl, ($C_1$–$C_4$)alkoxy or halogen;

$R^2$ is ($C_1$–$C_4$)alkyl optionally substituted with up to three fluoro atoms; and $R^3$ is ($C_3$–$C_7$)cycloalkyl; phenyl; phenyl substituted at the para position with ($C_1$–$C_4$)alkyl, halo or trifluoromethyl; phenyl substituted at the meta position with fluoro; or phenyl substituted at the ortho position with fluoro.

Glycogen phosphorylase dependent diseases or conditions refers to disorders which are mediated, initiated or maintained, in whole or in part, by the cleavage of the glycogen macromolecule by glycogen phosphorylase enzymes to release glucose-1-phosphate and a new shortened glycogen molecule. These disorders are ameliorated by reduction of or characterized by an elevation of glycogen phosphorylase activity. Examples include diabetes, hyperglycemia, hypercholesterolemia, hypertension, hyperinsulinemia, hyperlipidemia, atherosclerosis and myocardial ischemia.

The term glycogen phosphorylase inhibitor refers to any substance or agent or any combination of substances and/or agents which reduces, retards, or restrains the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis).

The term "treating" as used herein includes preventative (e.g., prophylactic), palliative and curative treatment.

By halo is meant chloro, bromo, iodo, or fluoro.

By alkyl is meant straight chain or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, hexyl and isohexyl.

By alkoxy is meant straight chain or branched saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, hexoxy and isohexoxy.

The expression "prodrug" refers to compounds that are drug precursors, which, following administration, release the drug in vivo via a chemical or physiological process (e.g., a prodrug on being brought to the physiological pH is converted to the desired drug form).

As used herein, the expressions "reaction-inert solvent" and "inert solvent" refers to a solvent or mixture of solvents which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates and solvates of the compounds of this invention, of the produgs of the compounds of this invention, and pharmaceutically acceptable salts of said hydrates and solvates are also included.

Other features and advantages will be apparent from the specification and claims which describe the invention.

DETAILED DESCRIPTION OF THE INVENTION

In general the compounds of Formula I can be made by processes which include processes known in the chemical arts, particularly in light of the description contained herein. Certain processes for the manufacture of Formula I compounds are provided as further features of the invention and are illustrated by the following reaction schemes.

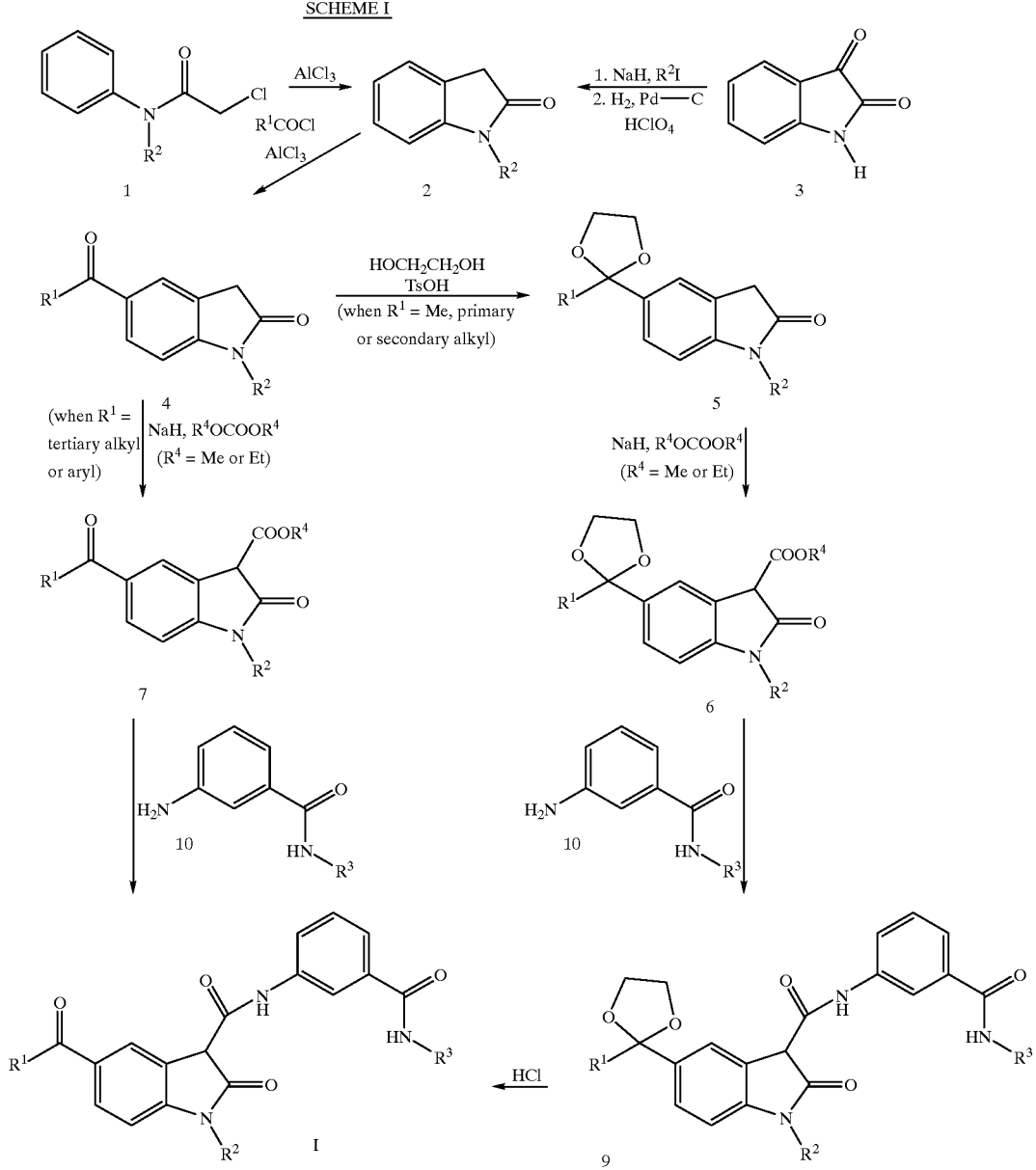

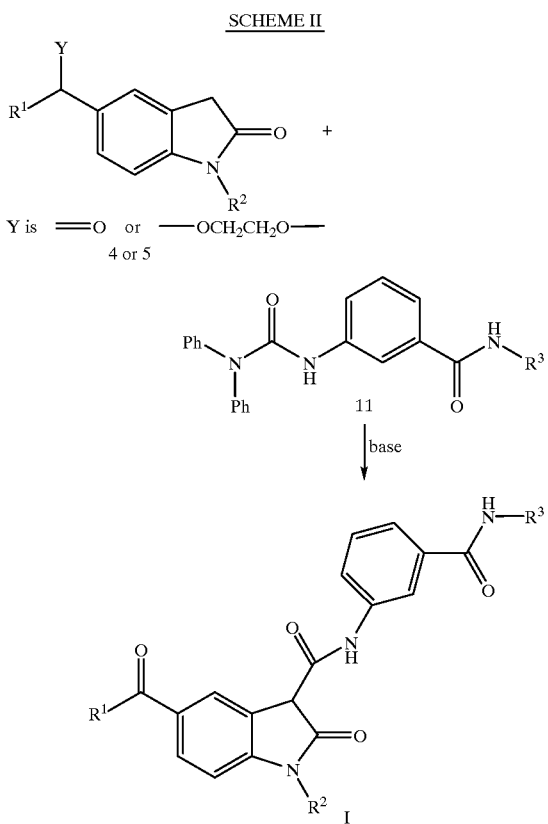

According to Scheme I, the compounds of Formula I wherein $R^1$, $R^2$ and $R^3$ are as defined above may be prepared by either of two general procedures. The procedures involve coupling a carboxylic acid or carboxylic acid ester derivative of formula 6 or 7 with an appropriate 3-substituted aniline derivative of formula 10. When the coupling is performed using a compound of formula 7, the immediate product is a compound of Formula I. When the coupling is performed using a compound of formula 6, which compound contains a protected ketone moiety, the intermediate result is a compound of formula 9 which is converted to a compound of Formula I by a subsequent deprotection step.

Typically, the deprotection of the formula 9 compounds may be carried out using methods well known to those skilled in the art, for example, methods described in "Protecting Groups in Organic Synthesis," Second Edition, T. W. Greene and P. G. M. Wuts, John Wiley and Sons, Inc., 1991. Generally, the compound of formula 9 is dissolved in a reaction inert solvent such as tetrahydrofuran and strong aqueous acid is added. The temperature of the reaction may be varied from 0° C. to 50° C. Generally, however, the reaction is performed at room temperature. The reaction is stirred until all or most of the starting material has reacted as determined by thin layer chromatography or other analytical technique well known to those skilled in the art. Ordinarily, the reaction is stirred for about fifteen minutes to twenty four hours and preferably for one hour. The resulting compound of Formula I is then isolated according to methods well known to those skilled in the art.

The coupling reaction referred to above is used to generate the compounds of Formula I directly from the compounds of formula 7 or to generate the compounds of formula 9 from the compounds of formula 6. The coupling reaction is most readily accomplished by reacting a carboxylic acid ester derivative of formula 6 or formula 7 with the appropriate aniline derivative of formula 10. Typically, a compound of formula 6 or formula 7 is dissolved in a reaction inert solvent and a compound of formula 10 is added. Molecular sieves (4 Å) are added and the reaction mixture is generally heated at the reflux temperature of the chosen solvent until the starting materials are no longer present as determined by thin layer chromatography or other analytical technique well known to those skilled in the art. The coupled product of formula 9 or Formula I is then isolated according to methods well known to those skilled in the art.

Alternatively, the compounds of Formula I may be prepared according to the procedure set forth in Scheme II. In this procedure, a compound of formula 5 wherein Y is as set forth in Scheme II is reacted with an activated amide such as a N,N-diphenylureido derivative in the presence of a base to form the compound of Formula I. Typically, the compound of formula 5 wherein Y is =O (when $R^1$ is tertiary alkyl or aryl) or —OCH$_2$CH$_2$O— (when $R^1$ is primary or secondary alkyl) and $R^1$ and $R^2$ are as described above is dissolved in a suitable solvent and is treated with a base which is strong enough to deprotonate the carbon atom alpha to the carbonyl. The anion thus formed is treated with the activated amide compound and the reaction mixture is stirred for 16 hours to 7 days. Typically, the reaction is complete after stirring for three days. The reaction mixture is then acidifed to form the compound of Formula I directly.

The compounds of formulas 6 and 7 in Scheme I are prepared by standard acylation chemistry. For example, the compounds of formula 4 are acylated directly when $R^1$ is tertiary alkyl or aryl by reacting the compound of formula 4 under standard acylation conditions, e.g., base and acylating agent, to obtain the compound of formula 6. When $R^1$ is primary or secondary alkyl, the ketone moiety attached to the 5-position of the oxindole ring must be protected using standard ketone protecting groups as set forth in Greene and Wuts, supra. The protected compound of formula 5 is then acylated in the same manner as the compound of formula 4 to obtain the compound of formula 7. The acylation reaction described in this paragraph is readily carried out using procedures well known to those skilled in the art or by using methods analogous to those set forth in Melvin, U.S. Pat. No. 4,686,224, the teachings of which are incorporated herein by reference. Deprotection, if required, is performed using methods analogous to those described in Greene and Wuts, supra.

The compounds of formulas 1, 2, 3, 4 and 10 are prepared according to methods well known to those skilled in the art. Further, the starting materials and reagents for the above described reaction schemes are also readily available from commercial sources or can be readily synthesized by those skilled in the art using conventional methods of organic synthesis.

The compounds of Formula I have an asymmetric carbon atom and therefore are racemic mixtures of enantiomers when prepared from nonoptically active intermediates and reagents. Enantiomers can be separated by reacting the enantiomeric mixture with an appropriate optically active compound (e.g.,amine) to form a mixture of diastereomeric salts of the compound of Formula I and separating the diastereomers by crystallization or other method well known to those skilled in the art. It will be recognized by those skilled in the art that racemization of the optically active center may occur upon removal of the ammonium counterion. Therefore, when resolving the compounds of Formula I using optically active amine compounds, it is particularly advantageous to use pharmaceutically acceptable optically active amines such as naturally occurring amino acids protected as carboxylic acid esters or other pharmaceutically acceptable protected amino acids. Other physical resolution techniques such as chromatography are well known to those skilled in the art and these techniques may also be used to resolve the enantiomers of Formula I. All such diastereomers and enantiomers and mixtures thereof are considered as part of this invention.

It will be recognized that the compounds of this invention are acidic and they form a salt with a pharmaceutically acceptable cation. All such salts are within the scope of this invention and they can be prepared by conventional methods. Typical bases used to form such cationic salts are sodium hydroxide, sodium methoxide, sodium ethoxide, sodium hydride, potassium methoxide, magnesium hydroxide, calcium hydroxide, benzathine, choline, diethanolamine, piperazine and tromethamine. For example, the cationic salts can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, when the compounds of this invention form hydrates or solvates they are also within the scope of the invention.

The utility of the compounds of the present invention as medical agents in the treatment of metabolic diseases (such as are detailed herein) in animals, particularly mammals (e.g. humans) is demonstrated by the activity of the compounds of this invention in conventional assays and the in vitro and in vivo assays described below. Such assays also provide a means whereby the activities of the compounds of this invention can be compared with the activities of other known compounds. The results of these comparisons are useful for determining dosage levels in animals, particularly mammals, including humans, for the treatment of such diseases.

The three different purified glycogen phosphorylase (GP) isoenzymes, wherein glycogen phosphorylase is in the activated "a" state (referred to as glycogen phosphorylase a, or the abbreviation GPa), and referred to here as human liver glycogen phosphorylase a (HLGPa), human muscle glycogen phosphorylase a (HMGPa), and human brain glycogen phosphorylase a (HBGPa), can be obtained by the following procedures.

Expression and Fermentation

The HLGP cDNAs (obtained as described in Newgard et al., Proc. Natl. Acad. Sci., 1986, 83, 8132–8136; and Newgard et al., Proc. Natl. Acad. Sci., 1988, 263, 3850–3857, respectively) and HMGP cDNAs (obtained by screening a Stratagene (Stratagene Cloning Systems, La Jolla, Calif.) human muscle cDNA library with a polymerase chain reaction (PCR)-generated cDNA fragment based on information and methodology reported for isolation of the human skeletal muscle glycogen phosphorylase gene and partial cDNA sequence by Kubisch et al., Center for Molecular Neurobiology, University of Hamburg, Martinistrasse 85, Hamburg, 20246 Germany. Genbank (National Center for Biotechnology Information, National Institutes of Health, USA) Accession Numbers U94774, U94775, U94776 and U94777, submitted Mar. 20, 1997; Burke et al., Proteins, 1987, 2:177–187; and Hwang et al., Eur. J. Biochem., 1985, 152:267–274) are expressed from plasmid pKK233-2 (Pharmacia Biotech. Inc., Piscataway, N.J.) in $E.\ coli$ strain XL-1 Blue (Stratagene Cloning Systems, LaJolla, Calif.). The strain is inoculated into LB medium (consisting of 10 g tryptone, 5 g yeast extract, 5 g NaCl, and 1 ml 1N NaOH per liter) plus 100 mg/L ampicillin, 100 mg/L pyridoxine and 600 mg/L $MnCl_2$ and grown at 37° C. to a cell density of $OD_{550}$=1.0. At this point, the cells are induced with 1 mM isopropyl-1-thio-β-D-galactoside (IPTG). Three hours after induction the cells are harvested by centrifugation and cell pellets are frozen at −70° C. until needed for purification.

The HBGP cDNA can be expressed by several methodologies, for example, by the method described by Crerar, et al. (J. Biol. Chem. 270:13748–13756). The method described by Crerar, et al. (J. Biol. Chem. 270:13748–13756) for the expression of HBGP is as follows: the HBGP cDNA can be expressed from plasmid pTACTAC in $E.\ coli$ strain 25A6. The strain is inoculated into LB medium (consisting of 10 g tryptone, 5 g yeast extract, 5 g NaCl, and 1 ml 1N NaOH per liter) plus 50 mg/L ampicillin and grown overnight, then resuspended in fresh LB medium plus 50 mg/L ampicillin, and reinoculated into a 40× volume of LB/amp media containing 250 μM isopropyl-1-thio-β-D-galactoside (IPTG), 0.5 mM pyridoxine and 3 mM $MnCl_2$ and grown at 22° C. for 48–50 hours. The cells can then be harvested by centrifugation and cell pellets are frozen at −70° C. until needed for purification.

The HLGP cDNA is expressed from plasmid pBlueBac III (Invitrogen Corp., San Diego, Calif.) which is cotransfected with BaculoGold Linear Viral DNA (Pharmingen, San Diego, Calif.) into Sf9 cells. Recombinant virus is subsequently plaque-purified. For production of protein, Sf9 cells grown in serum-free medium (Sf-900 II serum free medium, Gibco BRL, Life Technologies, Grand Island, N.Y.) are infected at an moi of 0.5 and at a cell density of $2 \times 10^6$ cells/ml. After growth for 72 hours at 27° C., cells are centrifuged, and the cell pellets frozen at −70° C. until needed for purification.

Purification of Glycoen Phosphorylase Expressed in $E.\ coli$

The $E.\ coli$ cells in pellets described above are resuspended in 25 mM β-glycerophosphate (pH 7.0) with 0.2 mM DTT, 1 mM $MgCl_2$, plus the following protease inhibitors:

0.7 μg/mL Pepstatin A 0.5 μg/mL Leupeptin 0.2 mM phenylmethylsulfonyl fluoride (PMSF), and 0.5 mM EDTA, lysed by pretreatment with 200 μg/mL lysozyme and 3 μg/mL DNAase followed by sonication in 250 mL batches for 5×1.5 minutes on ice using a Branson Model 450 ultrasonic cell disrupter (Branson Sonic Power Co., Danbury Conn.). The $E.\ coli$ cell lysates are then cleared by centrifugation at 35,000×g for one hour followed by filtration through 0.45 micron filters. GP in the soluble fraction of the lysates (estimated to be less than 1% of the total protein) is purified by monitoring the enzyme activity (as described in GPa Activity Assay section, below) from a series of chromatographic steps detailed below.

Immobilized Metal Affinity Chromatography (IMAC)

This step is based on the method of Luong et al (Luong et al. Journal of Chromatography (1992) 584, 77–84.). 500 mL of the filtered soluble fraction of cell lysates (prepared from approximately 160–250 g of original cell pellet) are loaded onto a 130 mL column of IMAC Chelating-Sepharose (Pharmacia LKB Biotechnology, Piscataway, N.J.) which has been charged with 50 mM $CuCl_2$ and 25 mM β-glycerophosphate, 250 mM NaCl and 1 mM imidazole at pH 7 (equilibration buffer). The column is washed with equilibration buffer until the $A_{280}$ returns to baseline.

The sample is then eluted from the column with the same buffer containing 100 mM imidazole to remove the bound GP and other bound proteins. Fractions containing the GP activity are pooled (approximately 600 mL), and ethylenediaminetetraacetic acid (EDTA), DL-dithiothreitol (DTT), phenylmethylsulfonyl fluoride (PMSF), leupeptin and pepstatin A are added to obtain 0.3 mM, 0.2 mM, 0.2 mM, 0.5 μg/mL and 0.7 μg/mL concentrations respectively. The pooled GP is desalted over a Sephadex G-25 column (Sigma Chemical Co., St. Louis, Mo.) equilibrated with 25 mM Tris-HCl (pH 7.3), 3 mM DTT buffer (Buffer A) to remove imidazole and is stored on ice and subjected to a second chromatographic step (below) if necessary.

5'-AMP-Sepharose Chromatography

The desalted pooled GP sample (approximately 600 mL) is next mixed with 70 mL of 5'-AMP Sepharose (Pharmacia LKB Biotechnology, Piscataway, N.J.) which has been equilibrated with Buffer A (see above). The mixture is gently agitated for one hour at 22° C. then packed into a column and washed with Buffer A until the $A_{280}$ returns to baseline. GP and other proteins are eluted from the column with 25 mM Tris-HCl, 0.2 mM DTT and 10 mM adenosine 5'-monophosphate (AMP) at pH 7.3 (Buffer B). GP-containing fractions are pooled following identification by determining enzyme activity described below and visualizing the $M_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM β-glycerophosphate, 0.2 mM DTT, 0.3 mM EDTA, 200 mM NaCl, pH 7.0 buffer (Buffer C) and stored on ice until use.

Prior to use of the GP enzyme, the enzyme is converted from the inactive form as expressed in E.coli strain XL-1 Blue (designated GPb) (Stragene Cloning Systems, La Jolla, Calif.), to the active form (designated GPa) by the procedure described in Section (A) Activation of GP below.

Purification of Glycogen Phosphorylase Expressed in Sf9 Cells

The Sf9 cells in pellets described above are resuspended in 25 mM β-glycerophosphate (pH 7.0) with 0.2 mM DTT, 1 mM MgCl2, plus the following protease inhibitors:

0.7 μg/mL Pepstatin A
 0.5 μg/mL Leupeptin
 0.2 mM phenylmethylsulfonyl fluoride (PMSF), and
 0.5 mM EDTA, lysed by pretreatment with 3 μg/mL DNAase followed by sonication in batches for 3×1 minutes on ice using a Branson Model 450 ultrasonic cell disrupter (Branson Sonic Power Co., Danbury Conn.). The Sf9 cell lysates are then cleared by centrifugation at 35,000×g for one hour followed by filtration through 0.45 micron filters. GP in the soluble fraction of the lysates (estimated to be 1.5% of the total protein) is purified by monitoring the enzyme activity (as described in GPa Activity Assay section, below) from a series of chromatographic steps detailed below.

Immobilized Metal Affinity Chromatography (IMAC)

Immobilized Metal Affinity Chromatography is performed as described in the section above. The pooled, desalted GP is then stored on ice until further processed.

Activation of GP

Before further chromatography, the fraction of inactive enzyme as expressed in Sf9 cells (designated GPb) is converted to the active form (designated GPa) by the following procedure described in Section (A) Activation of GP below.

Anion Exchange Chromatography

Following activation of the IMAC purified GPb to GPa by reaction with the immobilized phosphorylase kinase, as described below, the pooled GPa fractions are dialyzed against 25 mM Tris-HCl, pH 7.5, containing 0.5 mM DTT, 0.2 mM EDTA, 1.0 mM phenylmethylsulfonyl fluoride (PMSF), 1.0 μg/mL leupeptin and 1.0 μg/mL pepstatin A. The fraction is then loaded onto a MonoQ Anion Exchange Chromatography column (Pharmacia Biotech. Inc., Piscataway, N.J.). The column is washed with equilibration buffer until the $A_{280}$ returns to baseline. The sample is then eluted from the column with a linear gradient of 0–0.25 M NaCl to remove the bound GP and other bound proteins. GP-containing fractions elute between 0.1–0.2 M NaCl range, as detected by monitoring the eluant for peak protein absorbance at $A_{280}$. The GP protein is then identified by visualizing the $M_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM N,N-bis-(2-hydroxyethyl)-2-aminoethanesulfonic acid (BES), 1.0 mM DTT, 0.5 mM EDTA, 5 mM NaCl, pH 6.8 buffer and stored on ice until use.

Determination of GP Enzyme Activity

A) Activation of GP: Conversion of GPb to GPa

Prior to the determination of GP enzyme activity, the enzyme is converted from the inactive form as expressed in E.coli strain XL-1 Blue (designated GPb) (Stragene Cloning Systems, La Jolla, Calif.), to the active form (designated GPa) by phosphorylation of GP using phosphorylase kinase as follows. The fraction of inactive enzyme as expressed in Sf9 cells (designated GPb) is also converted to the active form (designated GPa) by the follow procedure.

GP Reaction with Immobilized Phosphorylase Kinase

Phosphorylase kinase (Sigma Chemical Company, St. Louis, Mo.) is immobilized on Affi-Gel® 10 (BioRad Corp., Melvile, N.Y.) as per the manufacturer's instructions. In brief, the phosphorylase kinase enzyme (10 mg) is incubated with washed Affi-Gel® beads (1 mL) in 2.5 mL of 100 mM HEPES and 80 mM $CaCl_2$ at pH 7.4 for 4 hours at 4° C. The Affi-Gel® beads are then washed once with the same buffer prior to blocking with 50 mM HEPES and 1 M glycine methyl ester at pH 8.0 for one hour at room temperature. Blocking buffer is removed and replaced with 50 mM HEPES (pH 7.4), 1 mM β-mercaptoethanol and 0.2% $NaN_3$ for storage. Prior to use to convert GPb to GPa, the Affi-Gel® immobilized phosphorylase kinase beads are equilibrated by washing in the buffer used to perform the kinase reaction, consisting of 25 mM β-glycerophosphate, 0.3 mM DTT, and 0.3 mM EDTA at pH 7.8 (kinase assay buffer).

The partially purified, inactive GPb obtained from 5'-AMP-Sepharose chromatography above (from E. coli) or the mixture of GPa and GPb obtained from IMAC above (from Sf9 cells) is diluted 1:10 with the kinase assay buffer then mixed with the aforementioned phosphorylase kinase enzyme immobilized on the Affi-Gel® beads. NaATP is added to 5 mM and $MgCl_2$ to 6 mM. The resulting mixture is mixed gently at 25° C. for 30 to 60 minutes. The activated sample is removed from the beads and the percent activation of GPb by conversion to GPa is estimated by determining GP enzyme activity in the presence and absence of 3.3 mM AMP. The percentage of total GP enzyme activity due to GPa enzyme activity (AMP-independent) is then calculated as follows:

$$\% \text{ of total HLGPa} = \frac{\text{HLGP activity} - \text{AMP}}{\text{HLGP activity} + \text{AMP}}$$

Alternately, the conversion of GPb to GPa can be monitored by isoelectric focusing, based on the shift in electrophoretic mobility that is noted following conversion of GPb to GPa. GP samples are analyzed by isoelectric focusing (IEF) utilizing the Pharmacia PfastGel System (Pharmacia Biotech. Inc., Piscataway, N.J.) using precast gels (pI range 4–6.5) and the manufacturer's recommended method. The resolved GPa and GPb bands are then visualized on the gels by silver staining (2D-silver Stain II "Daiichi Kit", Daiichi Pure Chemicals Co., LTD., Tokyo, Japan). Identification of GPa and GPb is made by comparison to E. coli derived GPa and GPb standards that are run in parallel on the same gels as the experimental samples.

B) GPa Activity Assay

The disease/condition treating/preventing activities described herein of the compounds of this invention can be indirectly determined by assessing the effect of the compounds of this invention on the activity of the activated form of glycogen phosphorylase (GPa) by one of two methods; glycogen phosphorylase a activity is measured in the forward direction by monitoring the production of glucose-1-phosphate from glycogen or by following the reverse reaction, measuring glycogen synthesis from glucose-1-phosphate by the release of inorganic phosphate. All reactions are run in triplicate in 96-well microtiter plates and the change in absorbance due to formation of the reaction product is measured at the wavelength specified below in a MCC/340 MKII Elisa Reader (Lab Systems, Finland), connected to a Titertech Microplate Stacker (ICN Biomedical Co, Huntsville, Ala.).

To measure the GPa enzyme activity in the forward direction, the production of glucose-1-phosphate from glycogen is monitored by the multienzyme coupled general method of Pesce et al. [Pesce, M. A., Bodourian, S. H., Harris, R. C. and Nicholson, J. F. (1977) Clinical Chemistry 23, 1711–1717] modified as follows: 1 to 100 μg GPa, 10 units phosphoglucomutase and 15 units glucose-6-phosphate dehydrogenase (Boehringer Mannheim Biochemicals, Indianapolis, Ind.) are diluted to 1 mL in Buffer D (pH 7.2, 50 mM HEPES, 100 mM KCl, 2.5 mM ethyleneglycoltetraacetic acid (EGTA), 2.5 mM $MgCl_2$, 3.5 mM $KH_2PO_4$ and 0.5 mM dithiothreitol). 20 μl of this stock is added to 80 μl of Buffer D containing 0.47 mg/mL glycogen, 9.4 mM glucose, 0.63 mM of the oxidized form of nicotinamide adenine dinucleotide phosphate (NADP+). The compound to be tested is added as 5 μL of solution in 14% dimethylsulfoxide (DMSO) prior to the addition of the enzymes. The basal rate of GPa enzyme activity in the absence of inhibitors, e.g., a compound of this invention, is determined by adding 5 μL of 14% DMSO and a fully-inhibited rate of GPa enzyme activity is obtained by adding 20 μl of 50 mM of the positive control test substance, caffeine. The reaction is followed at room temperature by measuring the conversion of oxidized NADP+ to reduced NADPH at 340 nm.

To measure the GPa enzyme activity in the reverse direction, the conversion of glucose-1-phosphate into glycogen plus inorganic phosphate is measured by the general method described by Engers et al. [Engers, H. D., Shechosky, S. and Madsen, N. B. (1970) Can. J. Biochem. 48, 746–754] modified as follows: 1 to 100 ug GPa is diluted to 1 mL in Buffer E (pH 7.2, 50 mM HEPES, 100 mM KCl, 2.5 mM EGTA, 2.5 mM $MgCl_2$ and 0.5 mM dithiothreitol). 20 μl of this stock is added to 80 μl of Buffer E with 1.25 mg/mL glycogen, 9.4 mM glucose, and 0.63 mM glucose-1-phosphate. The compound to be tested is added as 5 μL of solution in 14% DMSO prior to the addition of the enzyme. The basal rate of GPa enzyme activity in the absence of added inhibitors, e.g., a compound of this invention, is determined by adding 5 μL of 14% DMSO and a fully-inhibited rate of GPa enzyme activity is obtained by adding 20 μL of 50 mM caffeine. This mixture is incubated at room temperature for 1 hour and the inorganic phosphate released from the glucose-1-phosphate is measured by the general method of Lanzetta et al. [Lanzetta, P. A., Alvarez, L. J., Reinach, P. S. and Candia, O. A. (1979) Anal. Biochem. 100, 95–97] modified as follows: 150 μL of 10 mg/mL ammonium molybdate, 0.38 mg/mL malachite green in 1 N HCl is added to 100 μl of the enzyme mix. After a 20 minute incubation at room temperature, the absorbance is measured at 620 nm.

The above assays carried out with a range of concentrations of test compound allows the determination of an $IC_{50}$ value (concentration of test compound required for 50% inhibition) for the in vitro inhibition of GPa enzyme activity by that test compound.

The compounds of this invention are readily adapted to clinical use as hypoglycemic agents. The hypoglycemic activity of the compounds of this invention can be determined by the amount of test compound that reduces glucose levels relative to a vehicle without test compound in male ob/ob mice. The test also allows the determination of an approximate minimal effective dose (MED) value for the in vivo reduction of plasma glucose concentration in such mice for such test compounds.

Since the concentration of glucose in blood is closely related to the development of diabetic disorders, the compounds of this invention, by virtue of their hypoglycemic action, prevent, arrest and/or regress diabetic disorders.

Five to eight week old male C57BL/6J-ob/ob mice (obtained from Jackson Laboratory, Bar Harbor, Me.) are housed five per cage under standard animal care practices. After a one week acclimation period, the animals are weighed and 25 microliters of blood are collected from the retro-orbital sinus prior to any treatment. The blood sample is immediately diluted 1:5 with saline containing 0.025% sodium heparin, and held on ice for metabolite analysis. Animals are assigned to treatment groups so that each group has a similar mean for plasma glucose concentration. After group assignment, animals are dosed orally each day for four days with the vehicle consisting of either: (1) 0.25% w/v methyl cellulose in water without pH adjustment; or (2) 0.1% Pluronic® P105 Block Copolymer Surfactant (BASF Corporation, Parsippany, N.J.) in 0.1% saline without pH adjustment. On day 5, the animals are weighed again and then dosed orally with a test compound or the vehicle alone. All compounds are administered in vehicle consisting of either: (1) 0.25% w/v methyl cellulose in water without pH adjustment; or (2)10% DMSO/0.1% Pluronic® in 0.1% saline without pH adjustment. The animals are then bled from the retro-orbital sinus three hours later for determination of blood metabolite levels. The freshly collected samples are centrifuged for two minutes at 10,000×g at room temperature. The supernatant is analyzed for glucose, for example, by the Abbott VP™ (Abbott Laboratories, Diagnostics Division, Irving, Tex.) and VP Super System®

Autoanalyzer (Abbott Laboratories, Irving, Tex.), using the A-Gent™ Glucose-UV Test reagent system (Abbott Laboratories, Irving, Tex.) (a modification of the method of Richterich and Dauwalder, Schweizerische Medizinische Wochenschrift, 101, 860 (1971)) (hexokinase method) using a 100 mg/dL standard. Plasma glucose is then calculated by the equation:

Plasma glucose (mg/dL)=Sample value×8.14 where 8.14 is the dilution factor, adjusted for plasma hematocrit (assuming the hematocrit is 44%).

The animals dosed with vehicle maintain substantially unchanged hyperglycemic glucose levels (e.g., greater than or equal to 250 mg/dL), animals treated with compounds having hypoglycemic activity at suitable doses have significantly depressed glucose levels. Hypoglycemic activity of the test compounds is determined by statistical analysis (unpaired t-test) of the mean plasma glucose concentration between the test compound group and vehicle-treated group on day 5. The above assay carried out with a range of doses of a test compound allows the determination of an approximate minimal effective dose (MED) value for the in vivo reduction of plasma glucose concentration.

The compounds of this invention are readily adapted to clinical use as hyperinsulinemia reversing agents, triglyceride lowering agents and hypocholesterolemic agents. Such activity can be determined by the amount of test compound that reduces insulin, triglycerides or cholesterol levels relative to a control vehicle without test compound in male ob/ob mice.

Since the concentration of cholesterol in blood is closely related to the development of cardiovascular, cerebral vascular or peripheral vascular disorders, the compounds of this invention, by virtue of their hypocholesterolemic action, prevent, arrest and/or regress atherosclerosis.

Since the concentration of insulin in blood is related to the promotion of vascular cell growth and increased renal sodium retention, (in addition to the other actions, e.g., promotion of glucose utilization) and these functions are known causes of hypertension, the compounds of this invention, by virtue of their hypoinsulinemic action, prevent, arrest and/or regress hypertension.

Since the concentration of triglycerides in blood contributes to the overall levels of blood lipids, the compounds of this invention, by virtue of their triglyceride lowering and/or free fatty acid lowering activity prevent, arrest and/or regress hyperlipidemia.

Free fatty acids contribute to the overall level of blood lipids and independently have been negatively correlated with insulin sensitivity in a variety of physiologic and pathologic states.

Five to eight week old male C57BL/6J-ob/ob mice (obtained from Jackson Laboratory, Bar Harbor, Me.) are housed five per cage under standard animal care practices and fed standard rodent diet ad libitum. After a one week acclimation period, the animals are weighed and 25 microliters of blood are collected from the retro-orbital sinus prior to any treatment. The blood sample is immediately diluted 1:5 with saline containing 0.025% sodium heparin, and held on ice for plasma glucose analysis. Animals are assigned to treatment groups so that each group has a similar mean for plasma glucose concentration. The compound to be tested is administered by oral gavage as an about 0.02% to 2.0% solution (weight/volume (w/v)) in either (1) 10% DMSO/ 0.1% Pluronic® P105 Block Copolymer Surfactant (BASF Corporation, Parsippany, N.J.) in 0.1% saline without pH adjustment or (2) 0.25% w/v methylcellulose in water without pH adjustment. Single daily dosing (s.i.d.) or twice daily dosing (b.i.d.) is maintained for 1 to, for example, 15 days. Control mice receive the 10% DMSO/0.1% Pluronic® P105 in 0.1% saline without pH adjustment or the 0.25% w/v methylcellulose in water without pH adjustment only.

Three hours after the last dose is administered, the animals are sacrificed by decapitation and trunk blood is collected into 0.5 mL serum separator tubes containing 3.6 mg of a 1:1 weight/weight sodium fluoride: potassium oxalate mixture. The freshly collected samples are centrifuged for two minutes at 10,000×g at room temperature, and the serum supernatant is transferred and diluted 1:1 volume/ volume with a 1 TIU/mL aprotinin solution in 0.1% saline without pH adjustment.

The diluted serum samples are then stored at –80° C. until analysis. The thawed, diluted serum samples are analyzed for insulin, triglycerides, free fatty acids and cholesterol levels. Serum insulin concentration is determined using Equate® RIA INSULIN kits (double antibody method; as specified by the manufacturer) purchased from Binax, South Portland, Me. The inter assay coefficient of variation is ≦10%. Serum triglycerides are determined using the Abbott VP™ and VP Super System® Autoanalyzer (Abbott Laboratories, Irving, Tex.), or the Abbott Spectrum CCX™ (Abbott Laboratories, Irving, Tex.) using the A-Gent™ Triglycerides Test reagent system (Abbott Laboratories, Diagnostics Division, Irving, Tex.) (lipase-coupled enzyme method; a modification of the method of Sampson, et al., Clinical Chemistry 21, 1983 (1975)). Serum total cholesterol levels are determined using the Abbott VP™ and VP Super System® Autoanalyzer (Abbott Laboratories, Irving, Tex.), and A-Gent™ Cholesterol Test reagent system (cholesterol esterase-coupled enzyme method; a modification of the method of Allain, et al. Clinical Chemistry 20, 470 (1974)) using 100 and 300 mg/dL standards. Serum free fatty acid concentration is determined utilizing a kit from Amano International Enzyme Co., Inc., as adapted for use with the Abbott VP™ and VP Super System® Autoanalyzer (Abbott Laboratories, Irving, Tex.), or the Abbott Spectrum CCX™ (Abbott Laboratories, Irving, Tex.). Serum insulin, triglycerides, free fatty acids and total cholesterol levels are then calculated by the equations, Serum insulin ($\mu$U/mL)=Sample value×2

Serum triglycerides (mg/dL)=Sample value×2

Serum total cholesterol (mg/dL)=Sample value×2

Serum free fatty acid ($\mu$Eq/L)=Sample value×2 where 2 is the dilution factor.

The animals dosed with vehicle maintain substantially unchanged, elevated serum insulin (e.g., 275 $\mu$U/mL), serum triglycerides (e.g., 235 mg/dl), serum free fatty acid (1500 mEq/mL) and serum total cholesterol (e.g., 190 mg/dL) levels, while animals treated with compounds of this invention generally display reduced serum insulin, triglycerides, free fatty acid and total cholesterol levels. The serum insulin, triglycerides, free fatty acid and total cholesterol lowering activity of the test compounds are determined by statistical analysis (unpaired t-test) of the mean serum insulin, triglycerides, or total cholesterol concentration between the test compound group and the vehicle-treated control group.

Activity in providing protection from ischemia (e.g., damage to heart tissue) for the compounds of this invention can be demonstrated in vitro according to procedures set forth in Butwell et al., Am. J. Physiol., 264, H1884–H1889, 1993 and Allard et al., Am. J. Physio., 1994, 267, H66–H74.

Experiments are performed using an isovolumic isolated rat heart preparation, essentially as described in the above-referenced article. Normal male Sprague-Dawley rats, male Sprague-Dawley rats treated to possess cardiac hypertrophy by an aortic banding operation, acutely diabetic male BB/W rats, or non-diabetic BB/W age matched control rats are pretreated with heparin (1000 U, i.p.), followed by pentobarbital (65 mg/kg, i.p.). After deep anesthesia is achieved as determined by the absence of a foot reflex, the heart is rapidly excised and placed into iced saline. The heart is retrogradely perfused through the aorta within 2 minutes. Heart rate and ventricular pressure are determined using a latex balloon in the left ventricle with high pressure tubing connected to a pressure transducer. The heart is perfused with a perfusate solution consisting of (mM) NaCl 118, KCl 4.7, $CaCl_2$ 1.2, $MgCl_2$ 1.2, $NaHCO_3$ 25 and glucose 11. The perfusion apparatus is tightly temperature-controlled with heated baths used for the perfusate and for the water jacketing around the perfusion tubing to maintain heart temperature at 37° C. Oxygenation of the perfusate is provided by a pediatric hollow fiber oxygenator (Capiax, Terumo Corp., Tokyo, Japan) immediately proximal to the heart. Hearts are exposed to perfusion solution with and without test compound for about 10 minutes or more, followed by 20 minutes of global ischemia and 60 minutes of reperfusion in the absence of the test compound. The heart beats of the control and test compound treated hearts are compared in the period following ischemia. The left ventricular pressure of the control and test compound treated hearts are compared in the period following ischemia. At the end of the experiment, hearts are also perfused and stained to determine the ratio of infarct area relative to the area at risk (% IA/AAR) as described below.

The therapeutic effects of the compounds of this invention in preventing heart tissue damage otherwise resulting from an ischemic insult can also be demonstrated in vivo according to procedures set forth in Liu et al., Circulation, Vol. 84, No. 1, (July 1991), as described specifically herein. The in vivo assay tests the cardioprotection of a test compound relative to the control group which receives saline vehicle. As background information, it is noted that brief periods of myocardial ischemia followed by coronary artery reperfusion protects the heart from subsequent severe myocardial ischemia (Murry et al., Circulation 74:1124–1136, 1986). Cardioprotection, as indicated by a reduction in infarcted myocardium, can be induced pharmacologically using intravenously administered adenosine receptor agonists in intact, anesthetized rabbits studied as an in situ model of myocardial ischemic preconditioning (Liu et al., Circulation 84:350–356, 1991). The in vivo assay tests whether a compound can pharmacologically induce cardioprotection, i.e., reduced myocardial infarct size, when parenterally administered to intact, anesthetized rabbits. The effects of the compounds of this invention can be compared to ischemic preconditioning using the A1 adenosine agonist, $N^6$-1-(phenyl-2R-isopropyl) adenosine (PIA) that has been shown to pharmacologically induce cardioprotection in intact anesthetized rabbits studied in situ (Liu et al., Circulation 84:350–356, 1991). The exact methodology is described below.

Surgery: New Zealand White male rabbits (3–4 kg) are anesthetized with sodium pentobarbital (30 mg/kg, i.v.). A tracheotomy is performed via a ventral midline cervical incision and the rabbits are ventilated with 100% oxygen using a positive pressure ventilator. Catheters are placed in the left jugular vein for compound administration and in the left carotid artery for blood pressure measurements. The hearts are then exposed through a left thoracotomy and a snare (00 silk) placed around a prominent branch of the left coronary artery. Ischemia is induced by pulling the snare tight and clamping it in place. Releasing the snare allowed the affected area to reperfuse. Myocardial ischemia is evidenced by regional cyanosis; reperfusion was evidenced by reactive hyperemia.

Protocol: Once arterial pressure and heart rate has been stable for at least 30 minutes the experiment is started. Ischemic preconditioning is induced by twice occluding the coronary artery for 5 min followed by a 10 min reperfusion. Pharmacological preconditioning is induced by twice infusing a test compound over, for example, 5 minutes and allowing 10 minutes before further intervention or by infusing the adenosine agonist, PIA (0.25 mg/kg). Following ischemic preconditioning, pharmacological preconditioning or no conditioning (unconditioned, vehicle control) the artery is occluded for 30 minutes and then reperfused for two hours to induce myocardial infarction. The test compound and PIA are dissolved in saline or other suitable vehicle and delivered at 1 to 5 ml/kg, respectively. Staining (Liu et al., Circulation 84:350–356, 1991): At the end of the 2 hour reperfusion period, the hearts are quickly removed, hung on a Langendorff apparatus, and flushed for 1 minute with normal saline heated to body temperature (38° C.). The silk suture used as the snare is then tied tightly to reocclude the artery and a 0.5% suspension of fluorescent particles (1–10 $\mu$m in diameter, obtained from Duke Scientific Corp., Palo Alto, Calif.) is infused with the perfusate to stain all of the myocardium except the area at risk (nonfluorescent ventricle). The hearts are then quickly frozen and stored overnight at –20° C. On the following day, the hearts are cut into 2 mm slices and stained with 1% triphenyl tetrazolium chloride (TTC). Since TTC reacts with living tissue, this stain differentiates between living (red stained) tissue, and dead tissue (unstained infarcted tissue). The infarcted area (no stain) and the area at risk (no fluorescent particles) are calculated for each slice of left ventricle using a pre-calibrated image analyzer. To normalize the ischemic injury for differences in the area at risk between hearts, the data is expressed as the ratio of infarct area vs. area at risk (% IA/AAR). All data are expressed as Mean±SEM and compared statistically using single factor ANOVA or unpaired t-test. Significance is considered as $p<0.05$.

The compounds of this invention can be tested for its utility in reducing or preventing ischemic injury in non-cardiac tissues, for example, the brain, or the liver, utilizing procedures reported in the scientific literature. The compounds of this invention can be administered by the preferred route and vehicle of administration and at the preferred time of administration either prior to the ischemic episode, during the ischemic episode, following the ischemic episode (reperfusion period) if included, or during any of the below-mentioned experimental stages.

The benefit of the compounds of this invention to reduce ischemic brain damage can be demonstrated, for example, in mammals using the method of Park, et al (Ann. Neurol. 1988;24:543–551). In brief, in the procedure of Park, et al. adult male sprague Dawley rats are anesthetized initially with 2% halothane, and thereafter by mechanical ventilation with a nitrous oxide-oxygen mixture (70%:30%) containing 0.5–1% halothane. A tracheostomy is then performed. The stroke volume of the ventilator is adjusted to maintain arterial carbon dioxide tension at approximately 35 mm Hg and adequate arterial oxygenation ($PaO_2>90$ mm Hg). Body temperature can be monitored by a rectal thermometer, and the animals can be maintained normothermic, if necessary, by external heating. The animals next undergo subtemporal craniectomy to expose the main trunk of the left middle cerebral artery (MCA) under an operating microscope, and the exposed artery is occluded with microbipolar coagulation to generate large ischemic lesions in the cerebral cortex and basal ganglia. After three hours of MCA occlusion, the rats are deeply anesthetized with 2% halothane and a thoracotomy is performed to infuse heparinized saline into the left ventricle. The effluent is collected via an incision of the right atrium. The saline washout is followed by approximately 200 ml of a fixative, e.g., 40% formaldehyde, glacial acetic acid and absolute methanol solution (FAM; 1:1:8, v/v/v), then the animals are decapitated and the head is stored in the fixative for 24 hours. The brain is then removed, dissected, processed, embedded in paraffin wax, and sectioned (approximately 100 sections per brain). The sections are then stained with hematoxylin-eosin or with a combination of cresyl violet and Luxol® (registered to Dow Chemical Co. and obtainable from Sigma Chemical Co., St. Louis, Mo.) fast blue, and examined by light microscopy to identify and quantitate the ischemic damage using an image analyzer (e.g. the Quantimet 720 Image Analyzer, Leica, Inc., Deerfield, Ill.). The ischemic volumes and areas are expressed in absolute units ($mm^3$ and $mm^2$) and as a percentage of the total region examined. The effect of the invention to reduce ischemic brain damage induced by MCA occlusion is noted based on a reduction in the area or volume of relative or absolute ischemic damage in the brain sections from the rats in the treatment group compared to brain sections from rats in a placebo-treated control group.

Other methods which could alternatively be utilized to demonstrate the benefit of the compounds of this invention to reduce ischemic brain damage include those described by Nakayama, et al. in Neurology 1988;38:1667–1673, Memezawa, et al. in Stroke 1992;23:552–559, Folbergrova, et al. in Proc. Nati. Acad. Sci 1995;92:5057–5059, or Gofti, et al. in Brain Res. 1990;522:290–307.

The benefit of the compounds of this invention to reduce ischemic liver damage can be demonstrated, for example, in mammals using the method of Yokoyama, et al. (Am. J. Physiol. 1990;258:G564–G570). In brief, in the procedure of Yokoyama, et al., fasted adult male Sprague Dawley rats are anesthetized with sodium pentobarbital (40 mg/kg i.p.), then the animals are tracheotomized and mechanically ventilated with room air. The liver is extirpated and placed in an environmental chamber maintained at constant temperature (37° C.), then perfused through the portal vein at a constant pressure of 15 cm $H_2O$ with a modified, hemoglobin-free Krebs-Henseleit buffer (in mM: 118 NaCl, 4.7 KCl, 27 $NaHCO_3$, 2.5 $CaCl_2$, 1.2 $MgSO_4$, 1.2 $KH_2PO_4$, 0.05 EDTA, and 11 mM glucose, plus 300 U heparin). The pH of the perfusate is maintained at 7.4 by gassing the buffer with 95% $O_2$—5% $CO_2$. Each liver is perfused at a flow rate of 20 ml/min in a single-pass manner for a 30 min washout and equilibration period (preischemic period), followed by a 2 hour period of global ischemia, and then a 2 hour period of reperfusion under conditions identical to the preischemic period. Aliquots (20 ml) of the perfusate are collected during the preischemic period, immediately after the occlusive ischemic period, and every 30 min of the 2 hour reperfusion period. The perfusate samples are assayed for the appearance of hepatocellular enzymes, for example, aspartate amino-transferase (AST), alanine amino-transferase (ALT), and lactate dehydrogenase (LDH), which are taken to quantitatively reflect the degree of ischemic liver tissue damage during the procedure. AST, ALT, and LDH activities in the perfusate can be determined by several methods, for example, by the reflectometry method using an automatic Kodak Ektachem 500 analyzer reported by Nakano, et al. (Hepatology 1995;22:539–545). The ability of the compounds of this invention to reduce ischemic liver damage induced by occlusion is noted based on a reduction in the release of hepatocellular enzymes immediately following the occlusive period and/or during the postischemic-reperfusion period in the perfused livers from the rats in the treatment group compared to perfused livers from rats in a placebo-treated control group.

Other methods and parameters which could alternatively be utilized to demonstrate the benefit of the compounds of this invention to reduce ischemic liver damage include those described by Nakano, et al. (Hepatology 1995;22:539–545).

Administration of the compounds of this invention can be via any method which delivers a compound of this invention preferentially to the liver and/or cardiac tissues. These methods include oral routes, parenteral, intraduodenal routes, etc. Generally, the compounds of the present invention are administered in single (e.g., once daily) or multiple doses.

However, the amount and timing of compound(s) administered will, of course, be dependent on the particular disease/condition being treated, the subject being treated, on the severity of the affliction, on the manner of administration and on the judgment of the prescribing physician. Thus, because of subject to subject variability, the dosages given below are a guideline and the physician may titrate doses of the drug to achieve the activity (e.g., glucose lowering activity) that the physician considers appropriate for the subject. In considering the degree of activity desired, the physician must balance a variety of factors such as starting level, other risk (cardiovascular) factors, presence of preexisting disease, and age of the subject and the subject's motivation.

In general an effective dosage for the compounds of this invention, for example in the blood glucose, triglycerides, free fatty acid and cholesterol lowering activities and hyperinsulinemia reversing activities of the compounds of this invention is in the range of 0.005 to 50 mg/kg/day, preferably 0.01 to 25 mg/kg/day and most preferably 0.1 to 15 mg/kg/day.

Generally, the compounds of this invention are administered orally, but parenteral administration (e.g., intravenous, intramuscular, subcutaneous or intramedullary) may be utilized, for example, where oral administration is inappropriate for the instant target or where the subject is unable to ingest the drug. Topical administration may also be indicated, for example, where the subject is suffering from gastrointestinal disorders or whenever the medication is best applied to the surface of a tissue or organ as determined by the attending physician.

The compounds of the present invention are generally administered in the form of a pharmaceutical composition comprising at least one of the compounds of this invention together with a pharmaceutically acceptable carrier or diluent. Thus, the compounds of this invention can be administered individually or together in any conventional oral, parenteral or transdermal dosage form.

For oral administration, a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Since the present invention has an aspect that relates to a combination of active ingredients which may be administered separately, the invention also relates to combining separate pharmaceutical compositions in kit form. The kit comprises two separate pharmaceutical compositions: a compound of Formula I, a prodrug thereof or a pharmaceutically acceptable salt of said compound or said prodrug and a second compound as described above. The kit comprises container means for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the dosage form so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several tablets or capsules to be taken on a given day. Also, a daily dose of a Formula I compound, a prodrug thereof or a pharmaceutically acceptable salt of said compound or said prodrug can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout or audible reminder signal which, for example, reads out the date that the last daily dose has been taken and/or reminds one when the next dose is to be taken.

Methods of preparing various pharmaceutical compositions with a certain amount of active ingredient are known, or will be apparent in light of this disclosure, to those skilled in this art. For examples, see *Remington's Pharmaceutical Sciences*, Mack Publishing Company, Easton, Pa., 19th Edition (1990).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the disease/condition of the subject being treated, i.e., a glycogen phosphorylase dependent disease/condition.

TECHNIQUES

NMR spectra were recorded on a Varian XL-300 (Varian Co., Palo Alto, Calif.) or Bruker AM-300 spectrometer (Bruker Co., Billerica, Mass.) at about 23° C. at 300 MHz for proton and 75.4 mHz for carbon nuclei. Chemical shifts are expressed in parts per million downfield from trimethylsilane.

Column chromatography was performed with Amicon silica gel (30 uM, 60A pore size) (Amicon D Vision, W.R. Grace & Co., Beverly, Mass.) in glass columns under low nitrogen pressure. Unless otherwise specified, reagents were used as obtained from commercial sources. Dimethylformamide, 2-propanol, tetrahydrofuran, and dichloromethane used as reaction solvents were the anhydrous grade supplied by Aldrich Chemical Company (Milwaukee, Wis.). Microanalyses were performed by Schwarzkopf Microanalytical Laboratory, Woodside, N.Y. The terms "concentrated" and "coevaporated" refer to removal of solvent at water aspirator pressure on a rotary evaporator with a bath temperature of less than 45° C.

EXAMPLE 1

5-Acetyl-1-ethyl-2-oxo-2,3-dihydro-1H-indole-3-carboxylic acid (3-phenylcarbamoyl-phenyl)-amide

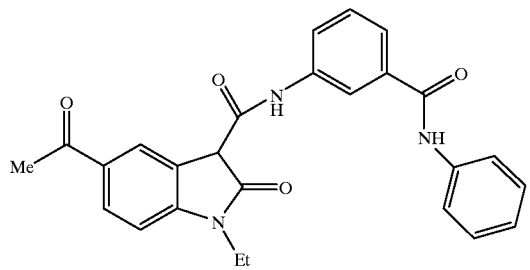

Step A. 1-Ethyl-5-(2-methyl-[1,3]dioxolan-2-yl)-2-oxo-2,3-dihydro-1H-indole-3-carboxylic acid (3-phenylcarbamoyl-phenyl)-amide. 1-Ethyl-5-(2-methyl-[1,3]dioxolan-2-yl)-2-oxo-2,3-dihydro-1H-indole-3-carboxylic acid methyl ester (3.6 g, 11.8 mmol) and 3-amino-N-phenyl-benzamide (5.0 g, 24 mmol) were combined in benzene (160 mL) in a flask fitted with a Soxhlet containing activated 4 Å molecular sieves. The mixture was heated to reflux for 30 min, then cooled, washed with 0.1 N HCl (2×30 mL), water and brine, dried over magnesium sulfate and concentrated in vacuo to a dark orange foam which was purified by flash-chromatography (chloroform/methanol, 20:1) to give a slightly orange foamy solid (3.75 g, 66%)

Step B. 5-Acetyl-1-ethyl-2-oxo-2,3-dihydro-1H-indole-3-carboxylic acid (3-phenylcarbamoyl-phenyl)-amide. To a solution of 1-ethyl-5-(2-methyl-[1,3]dioxolan-2-yl)-2-oxo-2,3-dihydro-1H-indole-3-carboxylic acid (3-phenylcarbamoyl-phenyl)-amide (the title compound of Example 1, Step A, 3.75 g, 7.8 mmol) in THF (70 mL) was added 2 N HCl (20 mL). The mixture was stirred at room temperature for 1 hour then poured into water (200 mL) and extracted with ethyl acetate. The extracts were washed with water and brine, dried over magnesium sulfate and concentrated in vacuo to afford an orange foam. The foam was dissolved in a small amount of ethyl acetate and precipitated with hexane to yield a tan solid, which was dried on high vacuum (mp 173–175° C., 2.5 g, 78%). Calculated for $C_{26}H_{23}N_3O_4$: C 70.74; H 5.25; N 9.52; found C70.91; H 5.56; N 9.25.

EXAMPLES 2–15

Examples 2 to 15 were prepared from the appropriate starting materials in a manner analogous to the method of Example 1, with variations in reaction time, temperature, and reagents as noted.

EXAMPLE 2

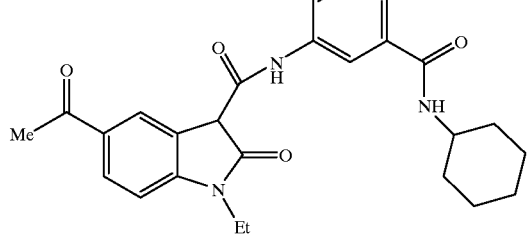

5-Acetyl-1-ethyl-2-oxo-2,3-dihydro-1H-indole-3-carboxylic acid (3-cyclohexylcarbamoyl-phenyl)-amide.

Prepared as in Example 1 from 1-ethyl-5-(2-methyl-[1,3]dioxolan-2-yl)-2-oxo-2,3-dihydro-1H-indole-3-carboxylic acid methyl ester and 3-amino-N-cyclohexyl-benzamide. Purified by trituration in ethyl acetate. mp 180° C. dec.

EXAMPLE 3

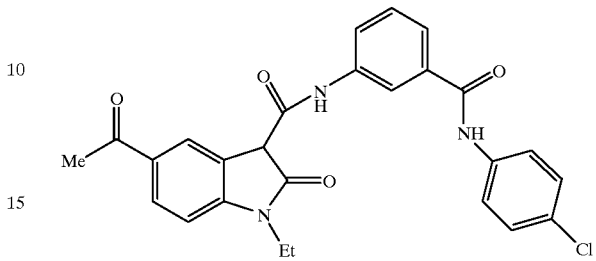

5-Acetyl-1-ethyl-2-oxo-2,3-dihydro-1H-indole-3-carboxylic acid [3-(4-chlorophenylcarbamoyl)-phenyl]-amide.

Prepared as in Example 1 from 1-ethyl-5-(2-methyl-[1,3]dioxolan-2-yl)-2-oxo-2,3-dihydro-1H-indole-3-carboxylic acid methyl ester and 3-amino-N-(4-chloro-phenyl)-benzamide. Recrystallized from ethyl acetate-hexanes. mp 119–121° C.

EXAMPLE 4

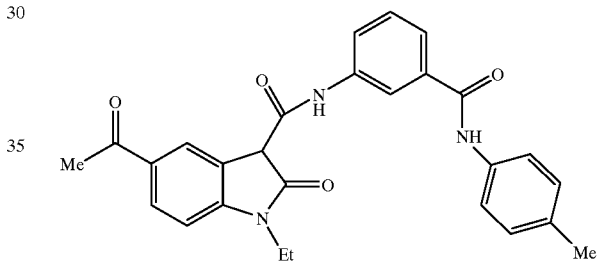

5-Acetyl-1-ethyl-2-oxo-2,3-dihydro-1H-indole-3-carboxylic acid (3-p-tolylcarbamoylphenyl)-amide.

Prepared as in Example 1 from 1-ethyl-5-(2-methyl-[1,3]dioxolan-2-yl)-2-oxo-2,3-dihydro-1H-indole-3-carboxylic acid methyl ester and 3-amino-N-(p-tolyl)-benzamide. Purified by trituration in ethyl acetate hexanes. mp 168 dec.

EXAMPLE 5

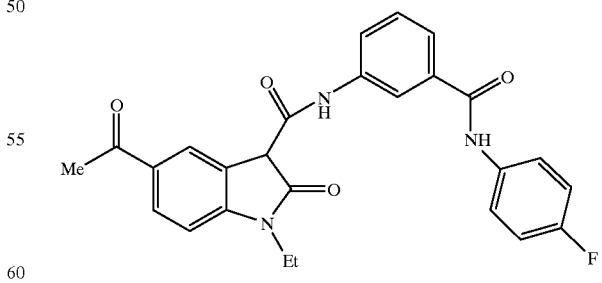

5-Acetyl-1-ethyl-2-oxo-2,3-dihydro-1H-indole-3-carboxylic acid [3-(4-fluorophenylcarbamoyl)-phenyl]-amide.

Prepared as in Example 1 from 1-ethyl-5-(2-methyl-[1,3]dioxolan-2-yl)-2-oxo-2,3-dihydro-1H-indole-3-carboxylic acid methyl ester and 3-amino-N-(4-fluoro-phenyl)- benzamide. Recrystallized from ethyl acetate-hexanes-benzene. Calculated for $C_{26}H_{22}FN_3O_4$: C 67.97; H 4.83; N 9.15; found C 68.34; H 5.31; N 8.80.

EXAMPLE 6

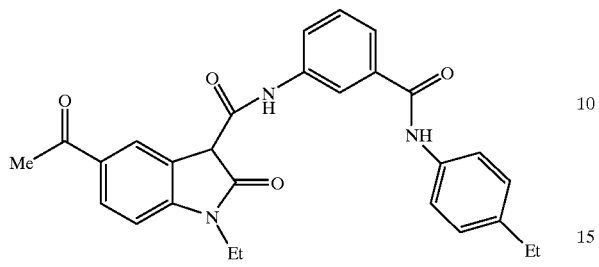

5-Acetyl-1-ethyl-2-oxo-2,3-dihydro-1H-indole-3-carboxylic acid [3-(4-ethylphenylcarbamoyl)-phenyl]-amide.

Prepared as in Example 1 from 1-ethyl-5-(2-methyl-[1,3] dioxolan-2-yl)-2-oxo-2,3-dihydro-1H-indole-3-carboxylic acid methyl ester and 3-amino-N-(4-ethyl-phenyl)-benzamide. Purified by chromatography (chloroform/methanol, 10:1). $^1$H NMR (DMSO-d6) δ 1.15 (m, 6 H), 2.5 (q, 2 H), 3.85 (q, 2 H), 6.85–8.3 (m, 11 H), 10.0 (s, 1 H), 11.1 (s, 1 H).

EXAMPLE 7

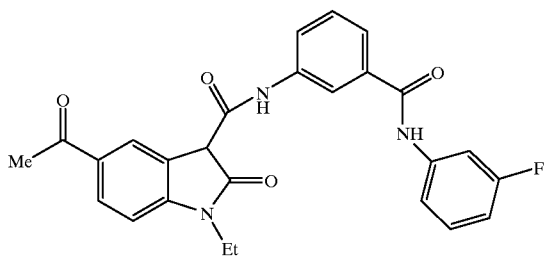

5-Acetyl-1-ethyl-2-oxo-2,3-dihydro-1H-indole-3-carboxylic acid [3-(3-fluorophenylcarbamoyl)-phenyl]-amide.

Prepared as in Example 1 from 1-ethyl-5-(2-methyl-[1,3] dioxolan-2-yl)-2-oxo-2,3-dihydro-1H-indole-3-carboxylic acid methyl ester and 3-amino-N-(3-fluoro-phenyl)-benzamide. $^1$H NMR (CDCl$_3$) δ 1.25 (t, 3 H), 2.6 (s, 3 H), 3.85 (q, 2 H), 4.45 (s, 1 H), 6.85–8.05 (m, 11 H), 8.3 (s, 1 H), 9.65 (s, 1 H).

EXAMPLE 8

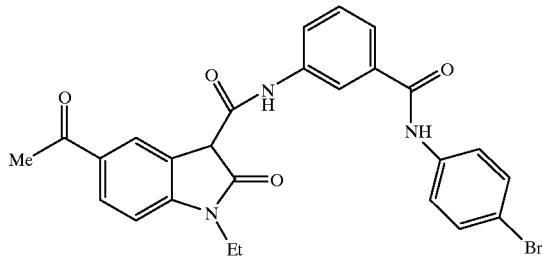

5-Acetyl-1-ethyl-2-oxo-2,3-dihydro-1H-indole-3-carboxylic acid [3-(4-bromophenylcarbamoyl)-phenyl]-amide.

Prepared as in Example 1 from 1-ethyl-5-(2-methyl-[1,3] dioxolan-2-yl)-2-oxo-2,3-dihydro-1H-indole-3-carboxylic acid methyl ester and 3-amino-N-(4-bromo-phenyl)-benzamide. mp 117–120° C.

EXAMPLE 9

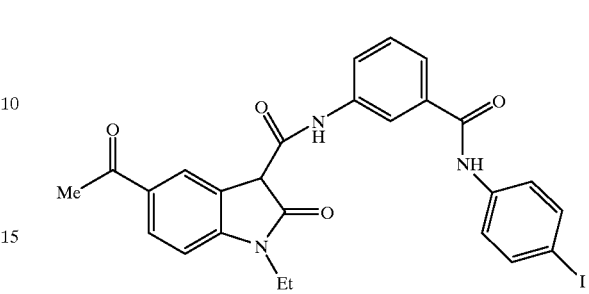

5-Acetyl-1-ethyl-2-oxo-2,3-dihydro-1H-indole-3-carboxylic acid [3-(4-iodophenylcarbamoyl)-phenyl]-amide.

Prepared as in Example 1 from 1-ethyl-5-(2-methyl-[1,3] dioxolan-2-yl)-2-oxo-2,3-dihydro-1H-indole-3-carboxylic acid methyl ester and 3-amino-N-(4-iodo-phenyl)-benzamide. mp 205–210° C. Calculated for $C_{26}H_{22}IN_3O_4$: C 55.04; H 3.91; N 7.41; found C 55.13; H 4.04; N 7.12.

EXAMPLE 10

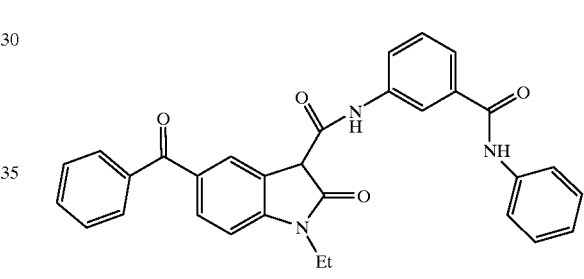

5-Benzoyl-1-ethyl-2-oxo-2,3-dihydro-1H-indole-3-carboxylic acid (3-phenylcarbamoyl-phenyl)-amide.

Prepared as in Example 1, Step A, from 5-benzoyl-1-ethyl-2-oxo-2,3-dihydro-1H-indole-3-carboxylic acid ethyl ester (U.S. Pat. No. 4,686,224) and 3-amino-N-phenyl-benzamide. Purified by trituration in ethyl acetate/hexanes. mp 129–135° C.

EXAMPLE 11

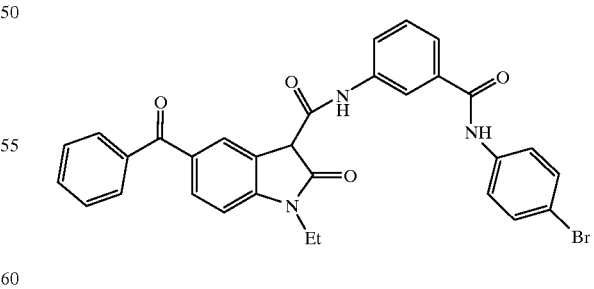

5-Benzoyl-1-ethyl-2-oxo-2,3-dihydro-1H-indole-3-carboxylic acid [3-(4-bromophenylcarbamoyl)-phenyl]-amide.

Prepared as in Example 1, Step A, from 5-benzoyl-1-ethyl-2-oxo-2,3-dihydro-1H-indole-3-carboxylic acid ethyl ester (U.S. Pat. No. 4,686,224) and 3-amino-N-(4-bromo-phenyl)-benzamide. Purified by flash-chromatography

EXAMPLE 12

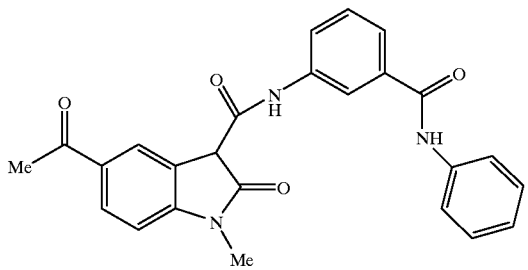

5-Acetyl-1-methyl-2-oxo-2,3-dihydro-1H-indole-3-carboxylic acid (3-phenylcarbamoyl-phenyl)-amide.

Prepared as in Example 1 from 1-methyl-5-(2-methyl-[1,3]dioxolan-2-yl)-2-oxo-2,3-dihydro-1H-indole-3-carboxylic acid methyl ester and 3-amino-N-phenyl-benzamide. Purified by trituration in hexanes/ethyl acetate. mp 178–179° C.

Calculated for $C_{25}H_{21}N_3O_4$: C 70.25; H 4.95; N 9.83; found C 69.89; H 4.79; N 9.69.

EXAMPLE 13

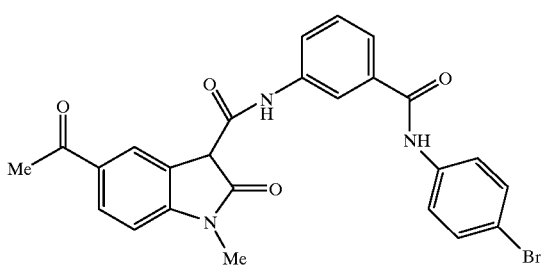

5-Acetyl-1-methyl-2-oxo-2,3-dihydro-1H-indole-3-carboxylic acid [3-(4-bromophenylcarbamoyl)-phenyl]-amide.

Prepared as in Example 1 from 1-methyl-5-(2-methyl-[1,3]dioxolan-2-yl)-2-oxo-2,3-dihydro-1H-indole-3-carboxylic acid methyl ester and 3-amino-N-(4-bromo-phenyl)-benzamide. Purified by flash-chromatography (hexanes/acetone, 1:1).

mp 234–236° C. Calculated for $C_{25}H_{20}BrN_3N_3O_4$: C 59.30; H 3.98; N 8.30; found C 59.12; H 4.15; N 8.08.

EXAMPLE 14

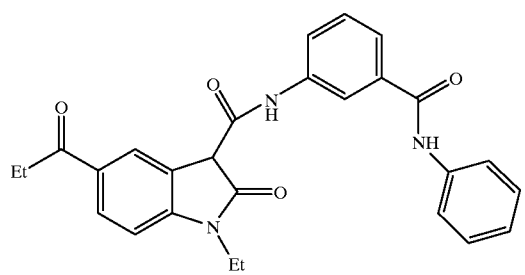

1-Ethyl-2-oxo-5-propionyl-2,3-dihydro-1H-indole-3-carboxylic acid (3-phenylcarbamoyl-phenyl)-amide.

Prepared as in Example 1 from 1-ethyl-5-(2-ethyl-[1,3]dioxolan-2-yl)-2-oxo-2,3-dihydro-1H-indole-3-carboxylic acid methyl ester and 3-amino-N-phenyl-benzamide. Purified by flash-chromatography (chloroform/methanol, 20:1) followed by trituration in hexanes/ethyl acetate. mp 179–180° C.

Calculated for $C_{27}H_{25}N_3O_4$: C 71.19; H 5.53; N 9.22; found C 70.79; H 5.73; N 8.79.

EXAMPLE 15

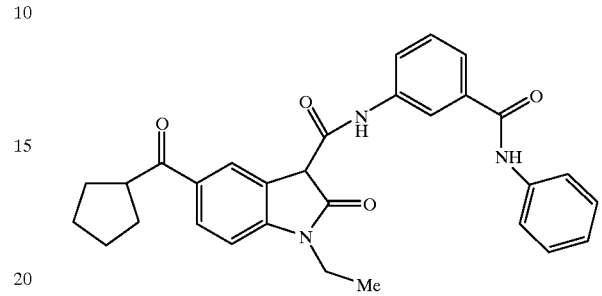

5-Cyclopentanecarbonyl-1-ethyl-2-oxo-2,3-dihydro-1H-indole-3-carboxylic acid (3-phenylcarbamoyl-phenyl)-amide.

Prepared as in Example 1 from 5-(2-cyclopentyl-[1,3]dioxolan-2-yl)-1-ethyl-2-oxo-2,3-dihydro-1H-indole-3-carboxylic acid ethyl ester and 3-amino-N-phenyl-benzamide. Purified by flash-chromatography (hexanes/acetone, 1:1) followed by trituration in ethyl acetate. mp 208–213° C.

EXAMPLE 16

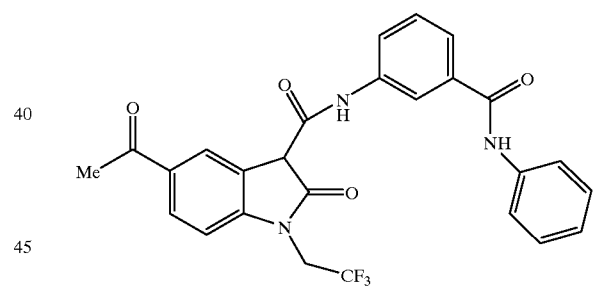

5-Acetyl-2-oxo-1-(2,2,2-trifluoro-ethyl)-2,3-dihydro-1H-indole-3-carboxylic acid (3-phenylcarbamoyl-phenyl)-amide.

Sodium hydride (0.13 g of a 60% suspension, 3.3 mmol) was added to a solution of 5-(2-methyl-[1,3]dioxolan-2-yl)-1-(2,2,2-trifluoroethyl)-1,3-dihydro-indol-2-one (0.5 g, 1.66 mmol) in HMPA (6 mL) and after 10 min 3-(3,3-diphenyl-ureido)-N-phenyl-benzamide (0.74 g, 1.8 mmol) was added. The reaction mixture was stirred for three days, acidified with 1 N HCl, poured into water and extracted with ethyl acetate. The combined extracts were washed with water and brine, dried over magnesium sulfate and concentrated in vacuo to a dark foam.

Trituration in ethyl acetate/hexanes gave the title compound as a colorless solid (124 mg, 15%, mp 197–203° C). Calculated for $C_{26}H_{20}F_3N_3O_4$: C 63.03; H 4.07; N 8.48; found C 62.83; H 4.32; N 8.47.

Preparation 1

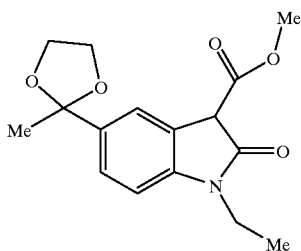

1-Ethyl-5-(2-methyl-[1,3]dioxolan-2-yl)-2-oxo-2,3-dihydro-1H-indole-3-carboxylic acid methyl ester.

Sodium (2.68 g, 112 mmol) was added to methanol (110 mL) in a 3-neck flask fitted with a reflux condenser, while controlling the temperature with an ice-bath. After dissolution dimethyl carbonate (9.4 mL, 112 mmol) was added followed by 1-ethyl-5-(2-methyl-[1,3]dioxolan-2-yl)-1,3-dihydro-indol-2-one (U.S. Pat. No. 4,686,224, 9.2 g, 37 mmol). The mixture was heated to reflux for 70 hours, then cooled, concentrated to about 25 mL, diluted with water, acidified to pH 7 with acetic acid and extracted twice with ethyl acetate. The combined extracts were washed with brine, dried over magnesium sulfate and concentrated in vacuo to an oily solid which was triturated in isopropyl ether, collected and dried (7.9 g, 70%).

Preparations 2–4

The compounds of Preparations 2 to 4 were prepared from the appropriate starting materials in a manner analogous to the method of Preparation 1.

Preparation 2

1-Methyl-5-(2-methyl-[1,3]dioxolan-2-yl)-2-oxo-2,3-dihydro-1H-indole-3-carboxylic acid methyl ester.

Prepared from 1-methyl-5-(2-methyl-[1,3]dioxolan-2-yl)-2,3-dihydro-indol-2-one, which was prepared as disclosed in U.S. Pat. No. 4,686,224.

Preparation 3

1-Ethyl-5-(2-ethyl-[1,3]dioxolan-2-yl)-2-oxo-2,3-dihydro-1H-indole-3-carboxylic acid methyl ester.

Prepared from 1-ethyl-5-(2-ethyl-[1,3]dioxolan-2-yl)-2,3-dihydro-indol-2-one, the title compound of Preparation 22.

Preparation 4

5-(2-Cyclopentyl-[1,3]dioxolan-2-yl)-1-ethyl-2-oxo-2,3-dihydro-1H-indole-3-carboxylic acid ethyl ester.

Preparaed from 5-(2-cyclopentyl-[1,3]dioxolan-2-yl)-1-ethyl-2,3-dihydro-indol-2-one, the title compound of Preparation 24.

Preparation 5

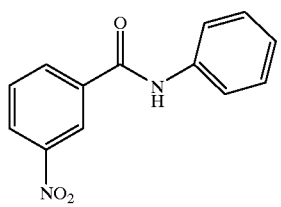

3-Nitro-N-phenyl-benzamide.

To a cooled (0° C.) solution of aniline (17 g, 180 mmol) and triethylamine (27 mL, 190 mmol) in dichloromethane (100 mL) was added a solution of 3-nitrobenzoyl chloride (30 g, 160 mmol) in dichloromethane (60 mL). The mixture was stirred for 15 min at 0° C. then overnight at room temperature. It was then poured into saturated sodium bicarbonate (1 L) and stirred vigorously for 15 min. The precipitate was collected, washed with water and dried (40 g, 100%).

Preparation 6

3-Amino-N-phenyl-benzamide.

10% Palladium on carbon (2.0 g) was added to a solution of 3-nitro-N-phenyl-benzamide (20 g, 83 mmol) in ethanol (225 mL) and the mixture was hydrogenated at 45 psi for 2 hours. The mixture was filtered through diatomaceous earth and concentrated to give a colorless solid (mp 118–120° C., 16 g, 90%).

Preparations 7–15

The compounds of Preparations 7 to 15 were prepared from the appropriate commercially available starting materials in a manner analogous to the methods of Preparations 5 and 6 performed sequentially.

Preparation 7
3-Amino-N-cyclohexyl-benzamide.

Preparation 8
3-Amino-N-(4-chloro-phenyl)-benzamide.

Preparation 9
3-Amino-N-(p-tolyl)-benzamide.

Preparation 10
3-Amino-N-(4-fluoro-phenyl)-benzamide.

Preparation 11
3-Amino-N-(4-ethyl-phenyl)-benzamide.

Preparation 12
3-Amino-N-(3-fluoro-phenyl)-benzamide.

Preparation 13
3-Amino-N-(4-bromo-phenyl)-benzamide.

Preparation 14
3-Amino-N-(4-iodo-phenyl)-benzamide.

Preparation 15
3-Amino-N-(3-methyl-phenyl)-benzamide.

Preparation 16

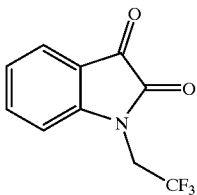

1-(2,2,2-Trifluoro-ethyl)-1H-indole-2.3-dione.

Sodium hydride (8.65 g of a 60% oil dispersion, 0.22 mol) was washed with hexane and suspended in hexamethylphosphoramide (200 mL). Isatin (29.4 g, 0.20 mol)) was added carefully. After the gas evolution subsided, 2,2,2-trifluoroethyl iodide (46.2 g, 0.22 mol) was added and the mixture was heated to 55° C. for 4 hours. The solution was cooled, diluted with water (1 L), and the precipitate was collected. The filtrate was acidified with 6 N HCl and a new precipitate formed and was collected. The combined solids were recrystallized from 95% ethanol. Yield 22.5 g (49%). mp 161–163° C.

Preparation 17

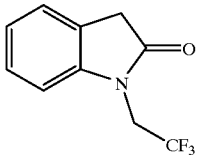

1-(2,2,2-Trifluoro-ethyl)-1,3-dihydro-indol-2-one.

A mixture of 1-(2,2,2-trifluoro-ethyl)-1H-indole-2,3-dione (9.2 g, 40 mmol) and 10% palladium on carbon (2.4 g) in acetic acid (100 mL) and 70% perchloric acid (6.4 mL, 80 mmol) was hydrogenated in a Parr apparatus for 22 hours. The mixture was filtered through diatomaceous earth, diluted with water (1.5 L) and the precipitate was collected and dried. mp 155–162° C. Yield 7.5 g (87%).

Preparation 18

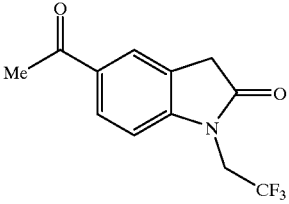

5-Acetyl-1-(2,2,2-trifluoro-ethyl)-1,3-dihydro-indol-2-one.

To a solution of 1-(2,2,2-trifluoro-ethyl)-1,3-dihydro-indol-2-one (2.0 g, 9.3 mmol) and acetyl chloride (0.86 mL, 12 mmol) in carbon disulfide (40 mL) was added aluminum trichloride (7.4 g, 56 mmol) by portions. The mixture was heated to reflux for 3 hours, then cooled. The liquid phase was decanted and the residue was quenched carefully with ice, then water. The solids were filtered, washed with water, dried and recrystallized from acetone/hexanes to give a pale pink solid, mp 170–171° C. Yield 1.23 g (51%).

Preparation 19

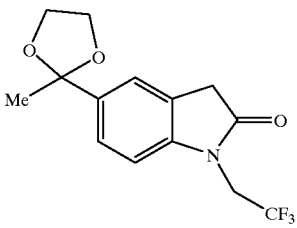

5-(2-Methyl-[1,3]dioxolan-2-yl)-1-(2,2,2-trifluoro-ethyl)-1,3-dihydro-indol-2-one.

A solution of 5-acetyl-1-(2,2,2-trifluoro-ethyl)-1,3-dihydro-indol-2-one (1.04 g, 4.0 mmol), ethylene glycol (1.37 mL, 24 mmol) and p-toluenesulfonic acid (10 mg) in benzene (25 mL) was heated to reflux for 4 hours in a flask fitted with a Dean-Stark trap. The solution was diluted with ethyl acetate, washed with saturated sodium bicarbonate, water and brine, dried over magnesium sulfate and concentrated in vacuo to an oil which solidified upon standing (1.19 g, 98%, mp 87–89° C.).

Preparation 20

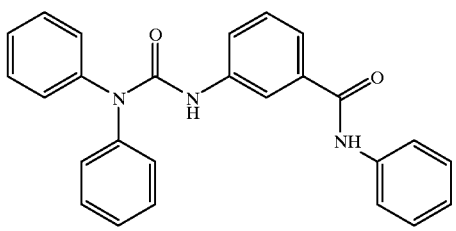

3-(3,3-Diphenyl-ureido)-N-phenyl-benzamide.

A mixture of 3-amino-N-phenylbenzamide (2.0 g, 9.4 mmol), diphenylcarbamoyl chloride (2.2 g, 9.4 mmol) and triethylamine (2.6 mL, 19 mmol) in ethanol (10 mL) was heated to reflux for 4.5 hours. The mixture was cooled and concentrated, water was added, the slurry was acidified with 1 N HCl and the solid was collected, washed with water, dried and recrystallized from acetone/hexanes, to give a colorless solid (1.63 g, 42%).

Preparation 21
1-Ethyl-5-Propionyl-2,3-dihydro-indol-2-one.

Prepared from readily available starting materials (N-ethyloxindole and propionyl chloride) in a manner analogous to that set forth in Preparation 18.

Preparation 22
1-Ethyl-5-(2-ethyl-[1,3]dioxolan-2-yl)-2,3-dihydro-indol-2-one.

Prepared from the title compound of Preparation 21 in a manner analogous to that set forth in Preparation 19.

Preparation 23
5-Cyclopentanecarbonyl-1-ethyl-2,3-dihydro-indol-2-one.

Prepared from readily available starting materials (N-ethyloxindole and cyclopentanecarbonyl chloride) in a manner analogous to that set forth in Preparation 18.

Preparation 24
5-(2-cyclopentyl-[1,3]dioxolan-2-yl)-1-ethyl-2,3-dihydro-indol-2-one.

Prepared from the title compound of Preparation 23 in a manner analogous to that set forth in Preparation 19.

It should be understood that the invention is not limited to the particular embodiments described herein, but that various changes and modifications may be made without departing from the spirit and scope of this novel concept as defined by the following claims.

We claim:

1. A compound of Formula I

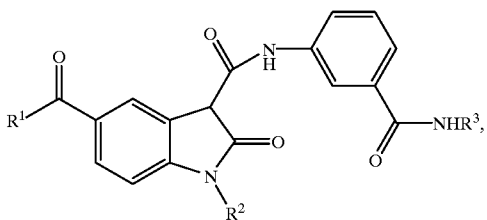

I a prodrug thereof or a pharmaceutically acceptable salt of said compound or said prodrug wherein:

$R^1$ is $(C_1-C_4)$alkyl, $(C_3-C_7)$cycloalkyl, phenyl or phenyl independently substituted with up to three $(C_1-C_4)$ alkyl, $(C_1-C_4)$alkoxy or halogen;

$R^2$ is $(C_1-C_4)$alkyl optionally substituted with up to three fluoro atoms; and $R^3$ is $(C_3-C_7)$cycloalkyl; phenyl; phenyl substituted at the para position with $(C_1-C_4)$alkyl, halo or trifluoromethyl; phenyl substituted at the meta position with fluoro; or phenyl substituted at the ortho position with fluoro.

2. A compound of claim 1, a prodrug thereof or a pharmaceutically acceptable salt of said compound or said prodrug, wherein $R^1$ is phenyl, $R^2$ is ethyl; and $R^3$ is phenyl, phenyl substituted at the para position with $(C_1-C_4)$alkyl, halo or trifluoromethyl, phenyl substituted at the meta position with fluoro, or phenyl substituted at the ortho position with fluoro.

3. A compound of claim 1, a prodrug thereof or a pharmaceutically acceptable salt of said compound or said prodrug, wherein $R^1$ is methyl and $R^2$ is ethyl.

4. A compound of claim 3, a prodrug thereof or a pharmaceutically acceptable salt of said compound or said prodrug, wherein $R^3$ is phenyl, phenyl substituted at the para position with $(C_1-C_4)$alkyl, halo or trifluoromethyl, phenyl substituted at the meta position with fluoro, or phenyl substituted at the ortho position with fluoro.

5. A compound of claim 4 selected from 5-acetyl-1-ethyl-2-oxo-2,3-dihydro-1H-indole-3-carboxylic acid (3-p-tolylcarbamoyl-phenyl)-amide; 5-acetyl-1-ethyl-2-oxo-2,3-dihydro-1H-indole-3-carboxylic acid (3-(4-bromophenylcarbamoyl-phenyl)-amide; and 5-acetyl-1-ethyl-2-oxo-2,3-dihydro-1H-indole-3-carboxylic acid (3-phenylcarbamoyl-phenyl)-amide.

6. The compound of claim 4 wherein $R^3$ is p-tolyl.

7. The compound of claim 4 wherein $R^3$ is 4-bromophenyl.

8. The compound of claim 4 wherein $R^3$ is phenyl.

9. A method for treating a glycogen phosphorylase dependent disease or condition in an animal, which comprises administering to said animal suffering from a glycogen phosphorylase dependent disease or condition a glycogen phosphorylase dependent disease or condition treating amount of a compound of claim 1, a prodrug thereof or a pharmaceutically acceptable salt of said compound or said prodrug.

10. The method as recited in claim 9 wherein the glycogen phorphorylase dependent disease or condition is hyperglycemia which comprises administering to said animal suffering from hyperglycemia a hyperglycemia treating amount of said compound, a prodrug thereof or a pharmaceutically acceptable salt of said compound or said prodrug.

11. The method of claim 9 wherein the glycogen phosphorylase dependent disease or condition is diabetes in an animal, which comprises administering to said animal suffering from diabetes a diabetes treating amount of said compound, a prodrug thereof or a pharmaceutically acceptable salt of said compound or said prodrug.

12. The method of claim 9 wherein the glycogen phosphorylase dependent disease or condition is hypercholesterolemia in an animal, which comprises administering to said animal suffering from hypercholesterolemia a hypercholesterolemia treating amount of said compound, a prodrug thereof or a pharmaceutically acceptable salt of said compound or said prodrug.

13. The method of claim 9 wherein the glycogen phosphorylase dependent disease or condition is atherosclerosis in an animal, which comprises administering to said animal suffering from or susceptible to atherosclerosis an atherosclerosis treating amount of said compound, a prodrug thereof or a pharmaceutically acceptable salt of said compound or said prodrug.

14. The method of claim 9 wherein the glycogen phosphorylase dependent disease or condition is hyperinsulinemia in an animal, which comprises administering to said animal suffering from hyperinsulinemia a hyperinsulinemia treating amount of said compound, a prodrug thereof or a pharmaceutically acceptable salt of said compound or said prodrug.

15. The method of claim 9 wherein the glycogen phosphorylase dependent disease or condition is hypertension in an animal, which comprises administering to said animal suffering from hypertension a hypertension treating amount of said compound, a prodrug thereof or a pharmaceutically acceptable salt of said compound or said prodrug.

16. The method of claim 9 wherein the glycogen phosphorylase dependent disease or condition is hyperlipidemia in an animal, which comprises administering to said animal suffering from hyperlipidemia a hyperlipidemia treating amount of said compound, a prodrug thereof or a pharmaceutically acceptable salt of said compound or said prodrug.

17. The method of claim 9 wherein the glycogen phosphorylase dependent disease or condition is tissue ischemic injury in an animal, which comprises administering to said animal at risk for tissue ischemic injury a tissue ischemic injury preventing amount of said compound, a prodrug thereof or a pharmaceutically acceptable salt of said compound or said prodrug.

18. The method of claim 9 wherein the glycogen phosphorylase dependent disease or condition is myocardial ischemic injury in an animal, which comprises administering to said animal at risk for myocardial ischemic injury a myocardial ischemic injury treating or preventing amount of said compound, a prodrug thereof or a pharmaceutically acceptable salt of said compound or said prodrug.

19. The method of claim 18 wherein said myocardial ischemic injury is perioperative myocardial ischemic injury.

20. A pharmaceutical composition which comprises a therapeutically effective amount of a compound of claim 1, a prodrug thereof or a pharmaceutically acceptable salt of said compound or said prodrug and a pharmaceutically acceptable carrier of diluent.

21. The pharmaceutical composition of claim 20 for the treatment of glycogen phosphorylase dependent diseases or conditions in animals, which comprises a glycogen phosphorylase dependent disease or condition treating amount of said compound, a prodrug thereof or a pharmaceutically acceptable salt of said compound or said prodrug and a pharmaceutically acceptable carrier or diluent.

22. A pharmaceutical composition which comprises a therapeutically effective amount of
   a) a glycogen phosphorylase inhibitor as recited in claim 1;
   b) an antidiabetic agent selected from insulin and insulin analogs;
   insulinotropin; sulfonylureas and analogs; biguanides; $\alpha_2$-antagonists and imidazolines; insulin secretagogues; glitazones; aldose reductase inhibitors; sorbitol dehydrogenase inhibitors; fatty acid oxidation inhibitors; $\alpha$-glucosidase inhibitors; $\beta$-agonists; phosphodiesterase inhibitors; lipid-lowering agents; antiobesity agents; vanadate and vanadiumn complexes and peroxovanadium complexes; amylin antagonists; glucagon antagonists; growth hormone secretagogues; gluconeogenesis inhibitors; somatostatin analogs; antilipotic agents; prodrugs of said antidiabetic agents and pharmaceutically acceptable salts of said antidiabetic agents and said prodrugs; and
   c) a pharmaceutically acceptable carrier or diluent.

23. A method for treating a glycogen phosphorylase dependent disease or condition in an animal, particularly a mammal, which comprises administering to said animal suffering from a glycogen phosphorylase dependent disease or condition a glycogen phosphorylase dependent disease or condition treating amount of a composition of claim 1.

* * * * *

UNITED STATES PATENT AND TRADEMARK OFFICE
CERTIFICATE OF CORRECTION

PATENT NO. : 5,998,463
DATED : December 7, 1999
INVENTOR(S) : Bernard Hulin and Reinhard Sarges It is certified that error appears in the above-identified patent and that said Letters Patent is hereby corrected as shown below:

Column 40,
Line 1, "vanadiumn" should read -- vanadium --;
Line 5, "antilipotic" should read -- antilipolytic --;
Line 11, "particularly a mammal" should be deleted;
Line 15, "claim 1" should read -- claim 22 --.

Signed and Sealed this

Twenty-eighth Day of August, 2001

Attest:

NICHOLAS P. GODICI
*Attesting Officer*    *Acting Director of the United States Patent and Trademark Office*